(12) United States Patent
De Vuyst et al.

(10) Patent No.: US 7,449,311 B2
(45) Date of Patent: Nov. 11, 2008

(54) **METHOD OF PRODUCING MACEDOCIN BY CULTURING *STREPTOCOCCUS MACEDONICUS***

(75) Inventors: Luc De Vuyst, Erembodegem (BE); Marina Georgalaki, Athens (GR); Effie Tsakalidou, Athens (GR)

(73) Assignee: Vrije Universiteit Brussel, Brussel (BE)

( * ) Notice: Subject to any disclaimer, the term of this patent is extended or adjusted under 35 U.S.C. 154(b) by 326 days.

(21) Appl. No.: 10/495,105

(22) PCT Filed: Nov. 21, 2002

(86) PCT No.: PCT/EP02/13075

§ 371 (c)(1),
(2), (4) Date: Sep. 3, 2004

(87) PCT Pub. No.: WO03/045987

PCT Pub. Date: Jun. 5, 2003

(65) Prior Publication Data

US 2005/0106662 A1   May 19, 2005

(30) Foreign Application Priority Data

Nov. 29, 2001 (EP) ................................. 01870264

(51) Int. Cl.
*C12P 21/00* (2006.01)
(52) U.S. Cl. ..................................... 435/71.3; 435/71.2
(58) Field of Classification Search .................. None
See application file for complete search history.

(56) References Cited

U.S. PATENT DOCUMENTS 5,445,835 A * 8/1995 Vedamuthu .................... 426/9

FOREIGN PATENT DOCUMENTS

| WO | WO 95/06736 | 3/1995 |
| WO | WO 96/32482 | 10/1996 |

OTHER PUBLICATIONS

Aktypis, et al. "Purification and Characterization of Thermophilin T, a Novel Bacteriocin Produced by *Streptococcus thermophilus* ACA-DC 0040," *Journal of Applied Microbiology*, vol. 84, pp. 568-576, 1998.

Georgalaki, et al. "Macedocin, a Food-Grade Lantibiotic Produced by *Streptococcus macedonicus* ACA-DC-198," *Applied and Environmental Microbiology*, pp. 5891-5903, Dec. 2002.

Georgalaki, et al. *"Biochemical Properties of *Streptococcus macedonicus* Strains Isolated from Greek Kasseri Cheese," *Journal of Applied Microbiology*, vol. 88, pp. 817-825, 2000.

Hynes, et al. "Cloning of the Gene Encoding Streptococcin A-FF22, a Novel Lantibiotic Produced by *Steptococcus pyogenes*, and Determination of Its Nucleotide Sequence," *Applied and Environmental Microbiology*, pp. 1969-1971, Jun. 1993.

Jack, et al. "Elucidation of the Structure of SA-FF22, a Lanthionine-Containing Antibacterial Peptide Produced by *Streptococcus pyogenes* Strain FF22," *European Journal of Biochemistry*, vol. 220, pp. 455-462, 1994.

McAuliffe, et al. "Lantibiotics: Structure, Biosynthesis and Mode of Action," *FEMS Microbiology Reviews*, vol. 25, pp. 285-308, 2001.

Roberts, et al. "Shelf-Life of Pasteurized Process Cheese Spreads Made from Cheddar Cheese Manufactured with a Nisin-Producing Starter Culture," *Journal of Dairy Science*, vol. 76, No. 7, pp. 1829-1836, Jul. 1993.

Taggs, et al. "Bacteriocin of a Group A Streptococcus: Partial Purification and Properties," *Antimicrobial Agents and Chemotherapy*, vol. 4, No. 3, pp. 214-221, 1973.

Tsakalidou, et al. Identification of *Streptococci* from Greek Kasseri Cheese and Description of *Streptococcus macedonicus* sp. nov., *International Journal of Systematic Bacteriology*, vol. 48, pp. 519-527, 1998.

* cited by examiner

*Primary Examiner*—Irene Marx
(74) *Attorney, Agent, or Firm*—Knobbe, Martens, Olson & Bear, LLP

(57) ABSTRACT

The invention relates to the field of bacteriocin producing microorganisms. The invention more specifically relates to the characterization of a novel food grade bacteriocin, namely a lantibiotic, named macedocin and produced by *Streptococcus macedonicus* ACA-DC 198. Macedocin inhibit a broad spectrum of lactic acid bacteria as well as several food spoilage and pathogenic bacteria, among others *Clostridium tyrobutyricum*, and is heat stable and active in a broad pH range. The invention further relates to the use of non-pathogenic microorganisms for producing macedocin in food fermentation processes, such as for preparing milk products, butter, cheese and fermented meat and vegetables, as well as in non-fermented food products such as raw meat, modified atmosphere-packed meat products, ready-to-eat meals, and canned food products, and its use for the preparation of functional starter cultures and cocultures.

1 Claim, 10 Drawing Sheets

(a)

(b)

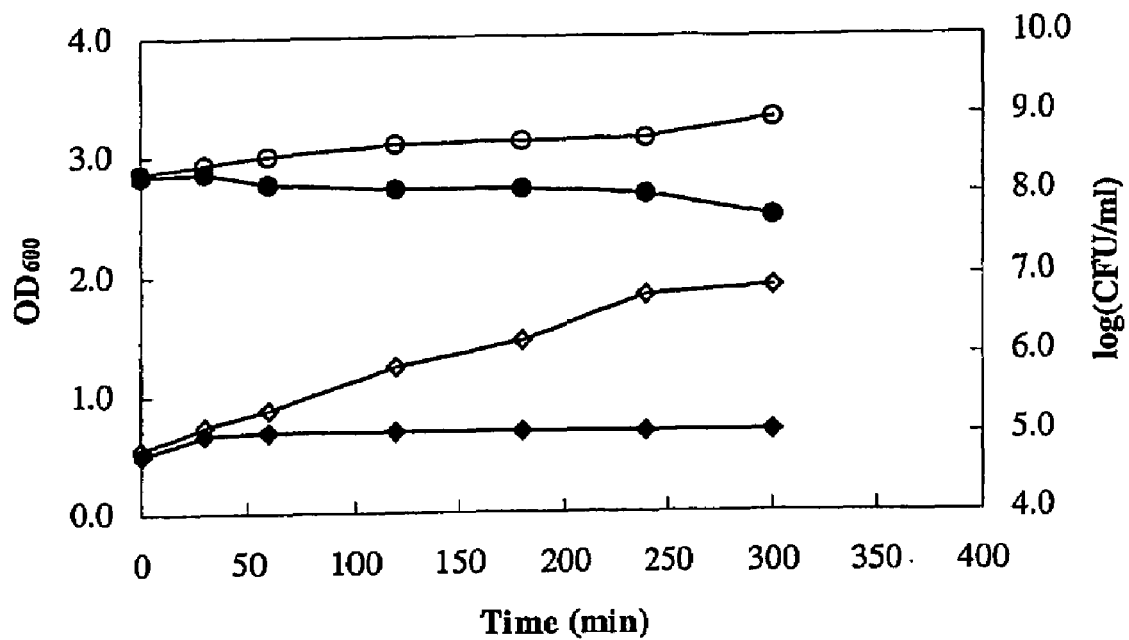
(c)
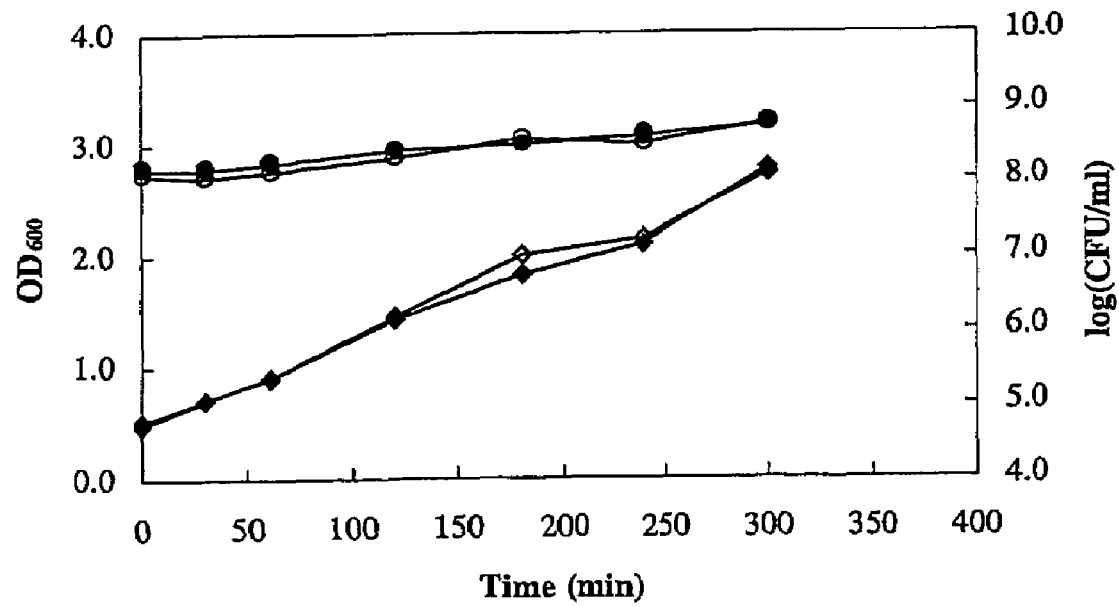
(d)
Figure 2 –continued–

(a)

(b)

| Purification step | Volume (ml) | Activity (AU/ml) | Protein concentration (mg/ml) | Total Activity (AU) | Specific activity (AU/mg) | Fold | Yield (%) |
|---|---|---|---|---|---|---|---|
| Crude | 455 | 160 | 2.1 | 72 800 | 76.2 | 1 | 100.0 |
| $(NH_4)_2SO_4$ Precipitation | 120 | 320 | 2.0 | 38 400 | 160.0 | 2.1 | 52.7 |
| Resource Q, pH 7.5 | 186 | 160 | 1.3 | 29 760 | 123.1 | 1.6 | 40.9 |
| Resource S, pH 5.5 | 40.5 | 320 | 0.4 | 12 960 | 800.0 | 10.5 | 17.8 |
| Resource RPC | 5.4 | 2 560 | 1.4 | 13 824 | 1 828.6 | 24.0 | 19.0 |
| Superdex Peptide | 7.5 | 152 | 0.06 | 1 140 | 2 533.3 | 33.2 | 1.6 |

METHOD OF PRODUCING MACEDOCIN BY CULTURING STREPTOCOCCUS MACEDONICUS

This application is the U.S. National Phase under 35 U.S.C. § 371 of International Application PCT/EP02/13075, filed Nov. 21, 2002, which claims priority of EP 01870264.7, filed Nov. 29, 2001. Each of the above applications are incorporated herein by reference in their entirety.

FIELD OF THE INVENTION

The invention relates to the field of bacteriocin producing microorganisms. The invention more specific relates to the characterization of a novel bacteriocin, namely a food grade lantibiotic, named macedocin, produced by *Streptococcus macedonicus*, and its use in the production of dairy products and starter cultures.

BACKGROUND OF THE INVENTION

In recent years, numerous food poisoning outbreaks involving various pathogens, along with the increasing concern about the preservation of minimally processed foods, have spurred growing awareness of the importance of food safety. This has prompted new approaches, on the one hand to inhibit food-borne pathogens, and on the other hand to prolong the shelf life of food products. In particular, there has been an increasing interest in the antimicrobial activity of lactic acid bacteria. Lactic acid bacteria have been used for centuries in the fermentation of foods, not only for flavor and texture development, but also because of their ability to produce antimicrobial compounds, which prevent the growth of spoilage and pathogenic microorganisms (De Vuyst and Vandamme 1994).

Among the antimicrobial compounds produced by lactic acid bacteria, bacteriocins are defined as proteinaceous compounds, which kill closely related bacteria (Tagg et al. 1976). Based on the observed structural characteristics, bacteriocins have been grouped into three classes. Class I (lantibiotics) and Class II (small, heat stable, non-lanthionine containing peptides) are the most abundant and thoroughly studied. In particular, the lantibiotics have attracted much attention in the last decade, because of the success of the well-characterized lantibiotic nisin as a food preservative. Indeed, the commercial exploitation of bacteriocins to date is mainly restricted to the food applications of nisin, the prototype lactic acid bacterium bacteriocin first discovered in 1928 by Rogers.

It is generally accepted that bacteriocins produced by lactic acid bacteria kill phylogenetically closely related bacteria, even though many characterized bacteriocins concur with this definition. For instance, it has become apparent that some have a broad host-range, inhibiting many different species and/or genera (McAuliffe et al. 2001). Indeed, both nisin and pediocin display a broad inhibitory spectrum. Due to this broad inhibitory spectrum and its lactic acid bacterium origin, until today nisin is the only bacteriocin used and approved in several foods worldwide.

There is however a growing need for new thermostable food grade bacteriocins which show activity in a broad pH range against a broad spectrum of microorganisms.

So far, streptococcal lantibiotics have been mainly isolated from oral streptococci. These bacteria are commonly found in the oral cavity and upper respiratory tract of humans and animals, although they may be isolated from almost any type of clinical specimen as well (Hardie 1986). Crossing the borders of pathogenicity, it is obvious that lantibiotic-producing oral streptococci have no chance to be used as such in food applications.

In spite of several problems concerning bacteriocin production in food environments still need to be addressed, the use of bacteriocin-producing cultures in food is of considerable advantage over using purified bacteriocin preparations.

Therefore it is one of the aims of the present invention to provide novel bacteriocins from safe microorganisms and use both said bacteriocins and said bacteriocin-producing strains in food industry.

SUMMARY OF THE INVENTION

The present invention relates to a novel food grade lantibiotic, named macedocin and produced by *Streptococcus macedonicus* ACA-DC 198. Macedocin possesses a molecular weight of 2 794.76±0.42, as determined by electrospray mass spectrometry. Partial N-terminal sequence analysis revealed 22 amino acid residues represented by SEQ ID NO 1. Macedocin inhibits a broad spectrum of lactic acid bacteria as well as several food spoilage and pathogenic bacteria, among others *Clostridium tyrobutyricum*. It displays a bacteriocidal effect as shown towards the most sensitive indicator strains like *Lactobacillus sakei* subsp. *sakei* LMG $13558^T$, while the producer strain itself displays auto-inhibition when grown under conditions that do not favor bacteriocin production. Macedocin is active in a broad pH range and is heat-stable. Inactivation and inhibition of the macedocin by proteolytic enzymes is variable.

The invention further relates to the use of *S. macedonicus* ACA-DC 198 in food fermentation such as processes producing milk products, butter, cheese, fermented meat, vegetables and cereals. The invention also relates to the use of *S. macedonicus* ACA-DC 198 for the preparation of functional starter cultures and adjunct cultures (co-cultures, e.g. as protective cultures) in food fermentation.

DETAILED DESCRIPTION OF THE INVENTION

The present inventors have shown that *S. macedonicus* ACA-DC 198, when grown in milk, produces an antimicrobial compound with a broad antibacterial spectrum.

*S. macedonicus* ACA-DC 198 is a strain isolated from Greek Kasseri cheese (ACA-DC refers to the Culture Collection of the Laboratory of Dairy Research, Agricultural University of Athens, Greece). *S. macedonicus* ACA-DC 198 is also known as *S. macedonicus* LAB 606 as deposited on Sep. 29, 1992, with the closed BCCM/LMG Culture Collection of the Laboratory of Microbiology Ghent, Ghent University, Belgium. The original deposit has been converted at the BCCM/LMG into a deposit under the Budapest treaty on Nov. 14, 2002, under the number LMG P-21771. Both deposits relate to the same sample of *S. macedonicus* ACA-DC 198.

According to a first embodiment the present invention relates to a method for producing a food grade lantibiotic, characterized in that a *Streptococcus macedonicus* ACA-DC strain is grown in milk. Preferably said milk is skimmed milk, semi-skimmed milk or full cream milk, more preferably said milk is supplemented with a nitrogen source. Interesting nitrogen sources for use in the methods for producing said food grade lantibiotic are yeast extract (0.01 to 10% (wt/vol)), tryptone (0.01 to 10% (wt/vol)), lactalbumin hydrolysate (0.01 to 10% (wt/vol)), about 0.3% casamino acids (wt/vol), or about 0.3% casein hydrolysate.

Preferred ranges for the amounts of yeast extract, tryptone or lactalbumin, which may be used as nitrogen source are from 0.025 to 6% (wt/vol), more preferably from 0.05 to 3% (wt/vol) and even more preferably from 0.3 to 1.5% (wt/vol).

According to a further embodiment, the invention relates to a food grade lantibiotic designated macedocin obtainable by production by *S. macedonicus* ACA-DC 198 in any of the above described milk media, said food grade lantibiotic characterised by:

a molecular weight of about 2795 as determined by electrospray ionization mass spectroscopy (e.g. 2794.76 exactly), inhibiting activity against a broad spectrum of microorganisms, heat-stability, and activity in a broad pH range.

In a further embodiment said food grade lantibiotic is characterized by an N-terminal amino acid sequence as represented in SEQ ID NO 1.

It has been found by the present inventors that the partial N-terminal amino acid sequence was identical to the respective amino acids of the lantibiotics SA-FF22 (FIG. 4) and SA-M49, both isolated from pathogenic *Streptococcus pyogenes* strains (Hynes et al. 1993; Hynes et al. 1994; Jack et al. 1994). Streptococcin SA-FF22 and SA-M49 possess a molecular weight of 2 794, and their amino acid sequences were deduced from the nucleotide sequence after cloning of the corresponding genes. For streptococcin SA-FF22, it was established that positions 8, 10, 13 and 17, which failed to yield amino acid signals during Edman sequencing, corresponded to the positions of threonine, serine, cysteine, and threonine, respectively, suggesting that streptococcin SA-FF22 contained one lanthionine and two β-methyl-lanthionine residues. This was further confirmed by chiral-phase gas chromatography (Jack et al. 1994). The fact that the Edman sequencing of the *S. macedonicus* bacteriocin failed to give signals at the same positions, while the rest of the N-terminal amino acid sequence shared 100% homology with streptococcin SA-FF22, along with the mass spectrometric data performed in the present work, contributed to the conclusion that the two molecules may be identical.

The *S. macedonicus* ACA-DC 198 bacteriocin retained activity in a broad pH range, remaining fully active between pH 4.0 and 9.0. Further, no activity was lost when maintained for 4 weeks at −70° C., −20° C., 4° C. or 30° C. The *S. macedonicus* ACA-DC 198 bacteriocin also showed a great heat stability since no loss of activity was observed even under sterilization conditions (20 min at 121° C.). These findings corresponded well with a lantibiotic structure. Indeed, other lantibiotics isolated from various streptococci share similar features, such as streptococcin SA-FF22 (Tagg et al. 1973), mutacin MT6223 (Loyola-Rodriguez et al. 1992) and mutacin II (Novák et al. 1994). However, the SA-FF22 streptococcin has not been reported to be stable under sterilization conditions and has been reported to loose 50% of its activity at a pH of 7 (Tagg et al., 1978), and to loose 75% of its activity when stored for 4 weeks at room temperature (Tagg et al., 1973). *S. pyogenes* belongs to the group A streptococci, which are important human pathogens producing numerous virulence factors, such as hemolysins (streptolysin-O and -S), erythrogenic toxins and pyrogenic exotoxins (Parker 1983). On the other hand, *S. macedonicus* is a food grade microorganism, isolated from cheese, exhibiting no potential pathogenicity traits. Therefore, the present inventors have named the novel *S. macedonicus* ACA-DC 198 bacteriocin, isolated and characterized in the present application, "macedocin", to clearly distinguish it from the *S. pyogenes* bacteriocins that are not food grade. This must avoid further confusion regarding food legislation and consumer awareness. However, the terms "bacteriocin" and "macedocin" as used herein to indicate the bacteriocin from the food grade bacterium *S. macedonicus* ACA-DC 198, are interchangeable. Furthermore, whenever "macedocin" is used herein, it should be understood that this term refers to the food grade bacteriocin of the invention and characterised as described earlier.

The term "bacteriocin" herein refers to (poly)peptides and proteins that inhibit one or more bacterial species. This includes, but is not limited to, (poly)peptides or proteins that were derived from specific strains of bacteria, (poly)peptides or proteins that were derived from other types of organisms or (poly)peptides or proteins developed through genetic engineering. The bacteriocin can be bacteriostatic or bacteriocidal or bacteriolytic; these concepts are known for the skilled person. Preferably, bacteriocins for use in the food industry are bacteriocidal.

The term "food grade" herein refers to the origin of the bacteriocin and the microorganism producing it. Food-grade indicates that a regulatory agency would consider the substance as coming from a non-spoiled "food" source or a food grade organism and therefore suitable for inclusion in food or food products. Organisms that are food-grade, such as lactic acid bacteria and other established genera of starter organisms, can be added directly to food without concern for pathogenicity.

Macedocin inhibited a broad spectrum of lactic acid bacteria as well as several food spoilage and pathogenic bacteria. Its inhibitory effect is species and/or strain dependent.

The invention thus relates to a food grade lantibiotic as described above wherein said lantibiotic shows an inhibitory activity profile such as shown in Table 1. It should be clear that the list of microorganisms as shown in Table 1 is non-exhaustive and may be completed by the skilled in the art upon testing more and other microorganisms.

The strongest activity of macedocin is against those microorganisms where the cell free supernatant of macedocin-producing *S. macedonicus* ACA-DC 198 is already able to inhibit growth of said microorganisms according to Example 2 and as shown in Table 1.

The invention thus relates to a food grade lantibiotic as described above wherein said lantibiotic inhibits at least one of the microorganisms indicated with a "+" or "+/−" notation in the column designated with "SUP" of Table 1, more preferably at least one of the microorganisms indicated with a "+" notation in the column designated with "SUP".

In another embodiment the invention relates to a food grade lantibiotic as described above wherein said lantibiotic inhibits at least one of the microorganisms indicated with a "+" or "+/−" notation in the column designated with "ASP" of Table 1, more preferably at least one of the microorganisms indicated with a "+" notation in the column designated with "ASP".

According to a more interesting embodiment, the food grade lantibiotic of the invention is active against at least one of the following group of species: *Bacillus cereus, Bacillus subtilis, Clostridium sporogenes, Clostridium tyrobutyricum, Enterococcus casseliflavus, Enterococcus durans, Enterococcus faecalis, Enterococcus faecium, Lactobacillus brevis, Lactobacillus sakei, Lactococcus garviae, Listeria innocua, Listeria ivanovii* and *Micrococcus luteus*. For specific applications, the food grade lantibiotic of the invention may be used for its activity against a species not mentioned in the above list, but mentioned in Table 1, wherein the results as presented herein, indicate that said species is sensitive to macedocin, the food grade lantibiotic of the present invention.

However, the invention also relates to a food grade lantibiotic which inhibits the activity of a microorganism which is not yet mentioned herein but which can be tested according to the methods provided in the Examples section.

It is well known in the art which food production process requires the inhibition of distinct undesired microorganisms. For instance, in cheese production, inhibition of microorganisms belonging to the genus *Clostridium* (hard cheeses) or *Listeria* (soft cheeses) is required. Therefore, the present invention provides several solutions for the inhibition of undesired microorganisms in the production or preservation of food.

The bacteriocin produced by *S. macedonicus* ACA-DC 198 is heat-stable. The term "heat-stability" means that no activity loss is observed after prolonged exposure to elevated temperatures. For instance macedocin produced by *S. macedonicus* ACA-DC 198 retained full activity after one week of incubation at 30° C. at various pH values from 4 to 9. Also no activity loss was observed after incubation for 1 h at 97° C., or even after 20 min at 121° C. and 2.1 atm of overpressure (autoclave).

The expression "activity in a broad pH range" means that the food grade lantibiotic or macedocin of the invention is active in acid and in alkaline pH. The macedocin remains fully active between pH 4.0 and 9.0, which means that the inhibition of microorganisms is 100%. It should be clear that at a pH lower than 4.0 and higher than 9.0 the macedocin is still active but to a lesser extent.

According to another embodiment, the invention relates to a method for producing a food grade lantibiotic as described above, wherein the *S. macedonicus* ACA-DC198 strain is grown under several of the conditions as shown in Table 2. It should be clear that the best conditions in which the *S. macedonicus* ACA-DC198 strain is grown are those wherein the bacteriocin (macedocin) production is at least 50 AU/ml, preferably at least 100 AU/ml, 150 AU/ml, 200 AU/ml, 250 AU/ml, more preferably at least 300 AU/ml, 350 AU/ml, most preferably at least 400 AU/ml. *S. macedonicus* ACA-DC198 strain grown in milk medium supplemented with yeast extract produces bacteriocin within a range from 50 AU/ml to at least 4000 AU/ml. Average bacteriocin production is in a range from 200 to 2500 AU/ml.

Although *S. macedonicus* ACA-DC 198 grew well in all media tested, macedocin was produced efficiently, only when the strain was grown in skim milk supplemented with nitrogen sources. It has been reported that synthetic or complex media, such as MRS, SM8 and TGE broth are mostly effective for the production of various bacteriocins (Biswas et al. 1991; De Vuyst 1995; Vignolo et al. 1995). Since the macedocin of the present invention is produced by a food grade organism, shows a broad inhibitory activity profile and demonstrates stability to freezing, storage at elevated temperatures and autoclaving, the present macedocin is particularly suited for use in the food industry. The surprisingly enhanced production of macedocin when *S. macedonicus* ACA-DC 198 is grown in a natural food system like milk as demonstrated by the present inventors makes the potential use of this strain as starter and as protective culture in food products more challenging, which is in contrast with other, bacteriocin-producing lactic acid bacterium strains.

One embodiment of the invention thus relates to the use of a non-pathogenic microorganism for the production of macedocin as a protective agent in food fermentation processes.

According to a further embodiment the macedocin is the food-grade antibiotic as described earlier by its physical and structural properties.

As used herein, the term "microorganism" or "organism" is used to refer to any species or type of microorganism, including but not limited to bacteria, yeast and other fungi, and protozoans.

According to a preferred embodiment, the non-pathogenic microorganism of the invention is a *S. macedonicus* strain, such as the *S. macedonicus* ACA-DC198 strain.

The invention more specific relates to the use of a *Streptococcus macedonicus* ACA-DC 198 strain in the food industry, for instance for the production of a food grade antibiotic as a protective agent in food fermentation processes.

The need for expanded use of bacteriocins is obvious, especially in the light of the consumers' demands for safe and minimally processed foods of adequate shelf life and convenience, and the global need for increasing the supply of health and safe foods. It is generally accepted that the use of bacteriocin-producing cultures in food is of considerable advantage over using purified bacteriocin preparations. The latter application requires extensive and costly purification schemes, toxicology tests, and may suggest a non-natural image of additives, for instance with respect to the applied concentration. In this meaning, the use of *S. macedonicus* as protective starter culture in food fermentation seems a straightforward option.

However, it is contemplated that in cases where it is not possible to add the microorganism (that produces macedocin, such as *S. macedonicus* ACA-DC 198) itself to the starter culture or to the food product, isolated macedocin derived from or originating from *S. macedonicus* ACA-DC 198 can be used instead. As shown in the Examples section, all of the properties of the macedocin (pH stability, heat-stability, inhibitory spectrum) have been tested when using macedocin in isolated form as well. The expression "derived from" or "originating from" means that it can be isolated from *S. macedonicus* ACA-DC 198, but that it may also be isolated from other *S. macedonicus* strains or it may be recombinantly produced in other microorganisms (or cells) or may be produced in the same or in any other matter. It should be clear that in case said isolated macedocin is to be used in food industry, said other microorganism is a food grade or a safe microorganism.

The production of fermented food is based on the use of starter cultures. The term "starter culture" refers to microorganisms that initiate a rapid acidification of the raw material, contributing to prolonged shelf life, an improved texture, and a desirable aromatic and sensorial profile of the end product. Through the use of biotechnology it is currently possible to suppress undesirable and express desirable properties of starter cultures. Recently, novel functional starter cultures are being developed. "Functional starter cultures" as used herein refer to starter cultures that possess at least one inherent, functional property. In the present invention "bacteriocin producing protective starter cultures" are examples of functional starter cultures.

The expression "protective starter culture" herein refers to a starter culture comprising an agent (such as a protective agent) that affords defense against a deleterious influence or which contributes to the microbial safety of the end product. In the present invention said (protective) agent can be understood as a substance or a microorganism producing a substance which kills or inhibits the growth of deleterious or unwanted microorganisms in the culture. Typical examples are microorganisms that produce antimicrobial substances, such as the bacteriocin or macedocin of the invention.

Therefore, the invention also relates to the use of *Streptococcus macedonicus* ACA-DC 198 for the production of a food grade lantibiotic to confer lantibiotic-producing properties to a starter culture.

In case *S. macedonicus* is added to aid to the fermentation/acidification of specific food products, the term "starter culture" is used herein. However, in case *S. macedonicus* only plays a minor role in the fermentation process, and its presence is mainly determined by its capacity to confer an additional functional property to the starter culture, the term "coculture" or "adjuvant culture" is mainly used. In case there is no fermentation process, *S. macedonicus* will be added only to confer additional (protective) properties to the food and the term "protective culture" is used.

A wide assortment of raw materials from animal (e.g. meat, fish and milk) as well as vegetal origin (e.g. vegetables, cereals, soy and coffee) is subjected to fermentation. Some typical examples of fermented foods and beverages and the type of microorganisms involved in their respective fermentation processes are presented in Table 3. A vast gamma of end products is obtained, including several dairy products (e.g. yogurt and cheese), bakery products (e.g. bread and sourdough), fermented meats (e.g. salami and sausage), fermented vegetables (e.g. pickles and sauerkraut), alcoholic beverages (e.g. wine and beer) etc.

The group of lactic acid bacteria includes the following genera: *Lactococcus, Lactobacillus, Paralactobacillus, Pediococcus, Tetragenococcus, Oenococcus, Carnobacterium, Leuconostoc, Weissella, Streptococcus, Enterococcus* and *Bifidobacterium*. As a typical feature, most of them grow rapidly in milk and form large quantities of lactic acid from lactose. They represent an important group of industrial microorganisms with a long and safe history of application and consumption in the production of fermented foods and beverages. Table 4 represents several examples of fermented foods and beverages and their associated lactic acid bacteria.

It should be clear that the present invention could be reduced to practice at least in each of the fermentation processes illustrated in Tables 3 and 4. The invention thus relates to the use of a non-pathogenic microorganism, for instance *S. macedonicus* ACA-DC 198 for the production of macedocin as a protective agent in at least one of the food fermentation processes with their associated microorganisms as shown in table 3 or 4.

The present invention thus also relates to the use of a macedocin-producing microorganism or culture, such as a culture of *S. macedonicus* ACA-DC 198 as a protective agent in dairy fermentations.

The term "culture" refers to any sample or specimen which is suspected of containing one or more microorganisms.

According to another embodiment the invention relates to a method for producing a dairy product comprising adding to the dairy product as starting materials a culture of a non-pathogenic microorganism, such as *S. macedonicus* ACA-DC 198, wherein said microorganism produces a food grade lantibiotic, such as the macedocin of the invention.

The invention also relates to a method for producing a fermented meat product, such as a sausage, comprising adding to the starting materials for fermentation a culture of a non-pathogenic microorganism, such as *S. macedonicus* ACA-DC 198, wherein said microorganism produces a food grade lantibiotic, such as the macedocin of the invention.

The invention further relates to a dairy product or a fermented meat product obtainable by any of the methods of the invention.

The invention further relates to a dairy product or a fermented meat product comprising *S. macedonicus* ACA-DC 198 chosen from cheese, yogurt, butter, kefir, sausage and salami or chosen from the fermented products shown in Table 3 or 4. It should be clear that whenever herein the expression "Fermented product" or "fermented food product" is used, each of the fermented food products mentioned in Table 3 or 4 could be meant, depending on the type of fermentation used. Furthermore it should be clear that the list of fermented food products and the list of microorganisms with fermenting capacities in Tables 3 and 4 is a non-exhaustive list.

Nowadays, attention of the consumer goes to the relation between food and health. As a consequence, the market of foods with health-promoting properties, so called functional foods, has known a remarkable growth over the last years. Moreover, the use of food additives has become a major point of discussion. The latter are regarded by the consumer as highly artificial and, consequently, as unnatural and unsafe. However, additives are in many cases essential to preserve foods from spoilage.

Recently, the use of functional starter cultures for the food fermentation industry is being explored. Examples are the insertion of carefully selected strains, such as lactic acid bacteria, as starter or co-culture in fermentation processes to help to achieve an in situ expression of the desired property, maintaining a perfectly natural product.

For instance, instead of adding potassium-nitrate or other substances to the milk in cheese-making to prevent late blowing (late loss), a non-pathogenic microorganism which produces the macedocin of the invention can be added, such as *S. macedonicus* ACA-DC 198. The inventors very interestingly found that, besides its properties concerning extreme pH and heat stability and its high activity levels achieved in milk through fermentation, it strongly inhibited *Clostridium tyrobutyricum* which is responsible for this phenomenon. "Late blowing" is characterized by the unwanted formation of large holes due to gas production by *Cl. tyrobutyricum*. The latter is often associated with silage feeding of cows. Spores of *Cl. tyrobutyricum* can survive pasteurization, which will lead to bacterial outgrowth and gas production during cheese maturation. Therefore the use of non pathogenic bacteriocin- or macedocin-producing lactic acid bacteria as functional starter or co-cultures represents an attractive alternative to the use of potassium nitrate in preventing the cheese from contamination by *Clostridia*.

Accordingly, an interesting embodiment of the invention relates to a method for preventing late gas-blowing in cheese production comprising the addition of a macedocin-producing non-pathogenic microorganism, such as *Streptococcus macedonicus* ACA-DC 198, to the initial cheese starter culture.

In an alternative embodiment, the invention relates to the use of a non-pathogenic microorganism species, such as *Streptococcus macedonicus* ACA-DC 198, for the production of macedocin to prevent clostridial spoilage in cheese.

The expression "clostridial spoilage" refers to food spoilage caused by microorganisms belonging to the genus *Clostridium*. The term "spoilage" as used herein refers to bacteria that act to spoil food and can be caused by several bacterial strains. Spoilage bacteria may grow and proliferate to such a degree that a food product is made unsuitable or undesirable or unsafe for human or animal consumption. Bacteria are able to proliferate on food surfaces, such as meat surfaces, by assimilating sugars and proteins on such surfaces. By metabolizing these components, spoilage bacteria create by-products including carbon dioxide, methane, nitrogenous compounds, butyric acid, propionic acid, lactic acid, formic acid, sulfur compounds, and other undesired gases and acids. The production of such by-products alters the color of meat surfaces, often turning meat from a red color to a brown, gray or green color. Gaseous by-products generated by spoilage bacteria also give spoiled meat an undesirable odor. The color and odor alterations of meat due to the growth of spoilage bacteria on a meat product's surface often makes such meat unsalable to consumers.

Chemical food additives such as nitrite, nitrate, sulphite, propionic acid, sorbic acid, and benzoic acid are commonly applied in food preservation technology. The addition of the food-grade lantibiotic or macedocin of the invention may provide an attractive alternative for the chemical products.

Therefore, the invention also relates to the use of a non-pathogenic microorganism, such as *Streptococcus macedonicus* ACA-DC 198, for the production of a lantibiotic, e.g. the macedocin of the invention, as a food preservative in fermented food products, for instance in pasteurized cheeses and cheese spreads, and as a food preservative in non-fermented food products, for instance in meats, vegetables, canned foods, modified-atmosphere-packed food products, and ready-to-eat meals.

It should be clear, it is preferable that the food grade lantibiotic referred to in any of the above described uses, is characterized by its physical and structural properties as described earlier. More specific, it is preferable that said food grade lantibiotic is active against at least one of the species from the group of the following species: *Bacillus cereus, Bacillus subtilis, Clostridium sporogenes, Clostridium tyrobutyricum, Enterococcus casseliflavus, Enterococcus durans, Enterococcus faecalis, Enterococcus faecium, Lactobacillus brevis, Lactobacillus sakei, Lactococcus garviae, Listeria innocua, Listeria ivanovii* and *Micrococcus luteus.*

According to another embodiment, the invention relates to a method for storing a non-fermented food product comprising adding to the product a co-culture or a protective culture or an adjunct culture of a macedocin-producing non-pathogenic microorganism, such as *Streptococcus macedonicus* ACA-DC 198.

In addition to the control of spoilage bacteria, another significant concern in the food processing industry is controlling the growth of pathogenic bacteria or non-starter bacteria. As used herein, the term "pathogenic bacteria" refers to any food poisoning or food spoiling organism that is capable of causing disease or illness in animals or humans. The term pathogenic bacteria will be understood to include bacteria that infect the food and thereby cause disease or illness, as well as bacteria that produce toxins that cause disease or illness. The proliferation of pathogenic bacteria on food products can cause severe illness and may be deadly, as demonstrated by the number of human fatalities caused by botulism and listeriosis.

As an alternative to chemical preservative agents, the antimicrobial activity displayed by several strains of lactic acid bacteria may help to combat microbial contamination of the food. The novel bacteriocin, named macedocin, isolated and characterized by the present inventors shows specific inhibitory activity against a broad range of microorganisms as demonstrated in the Examples and in Table 1.

Another embodiment of the invention thus relates to a method for controlling pathogenic and/or non-starter and/or undesired bacteria, in fermentation processes comprising adding to the starter culture a non-pathogenic microorganism for the production of a food-grade lantibiotic, such as the macedocin as described earlier.

A method for inhibiting the growth of at least one of the macedocin-sensitive microorganisms shown in Table 1 comprising the co-culturing of a *Streptococcus macedonicus* strain ACA-DC 198.

The term "non-starter" bacteria can also be replaced herein by "non-starter lactic acid bacteria" which includes for instance obligately heterofermentative *Lactobacilli* that are not intended to be comprised in the starter culture or fermentation of the specific end-product.

The term "undesired bacteria" as used herein, inherently refers to spoilage, non-starter or pathogenic bacteria.

According to a further embodiment the invention relates to a method for controlling non-starter lactic acid bacteria in cheese production comprising the addition of a macedocin-producing non-pathogenic microorganism, such as *S. macedonicus* ACA-DC 198 to the initial cheese starter culture.

Also embodied by the invention is a bacteriocidal or bacteriostatic or bacteriolytic composition active against at least one of the microorganisms in Table 1 comprising a macedocin-producing non-pathogenic microorganism, such as *S. macedonicus* ACA-DC 198.

In a more specific embodiment, the food grade lantibiotic comprised in the above composition is characterized by its physical and structural properties as described earlier and is preferable active against at least one of the species from the group of the following species: *Bacillus cereus, Bacillus subtilis, Clostridium sporogenes, Clostridium tyrobutyricum, Enterococcus casseliflavus, Enterococcus durans, Enterococcus faecalis, Enterococcus faecium, Lactobacillus brevis, Lactobacillus sakei, Lactococcus garviae, Listeria innocua, Listeria ivanovii* and *Micrococcus luteus.*

According to another embodiment the invention relates to a non-pathogenic microorganism for the production of a food grade lantibiotic, such as the macedocin of the invention, as a shelf-life extender in fermented food products, such as, but not limited to milk and milk products as well as in non-fermented food products such as, but not limited to raw meat, vegetables, modified-atmosphere-packed meat products, ready-to-eat meals, and canned food products.

According to another embodiment the invention relates to the use of a non-pathogenic microorganism for the preparation of functional starter cultures and cocultures.

As used herein the term "shelf life" means the period of time that a food product remains saleable to retail customers. The shelf life period of a certain food product is usually prolonged by refrigeration which largely arrests and/or retards the growth of pathogenic bacteria, and to a lesser extent, spoilage bacteria. After a certain period of time, however, refrigeration is no longer able to effectively control the proliferation of spoilage.

As already described earlier, the production of fermented food is based on the use of starter cultures. Interesting starter cultures are functional starter cultures that possess at least one inherent functional property. According to the present invention, a functional starter culture is a starter culture comprising a non-pathogenic microorganism, such as *S. macedonicus* ACA-DC 198 for the production of macedocin.

In an interesting embodiment, the invention thus relates to a starter culture, e.g. a functional starter culture, or a coculture comprising a non-pathogenic microorganism for the production of a food grade lantibiotic such as the macedocin of the invention. In a further embodiment said non-pathogenic microorganism is *Streptococcus macedonicus* ACA-DC 198, producing a food grade lantibiotic, e.g. macedocin, characterized by the physical and structural properties described earlier. Preferably, said food grade lantibiotic in the starter culture or coculture is active during fermentation against at least one of the species from the group of the following species: *Bacillus cereus, Bacillus subtilis, Clostridium sporogenes, Clostridium tyrobutyricum, Enterococcus casseliflavus, Enterococcus durans, Enterococcus faecalis, Enterococ-* cus faecium, Lactobacillus brevis, Lactobacillus sakei, Lactococcus garviae, Listeria innocua, Listeria ivanovii and Micrococcus luteus.

The present invention also relates to a starter culture as described above for the fermentation of a food product. Said food product can be any fermented food product as mentioned in Tables 3 or 4. In an interesting embodiment said food product is chosen from a milk product, yogurt, butter, a cheese or a sausage, a vegetable or a cereal.

The invention thus also relates to a method for producing a fermented meat product, a fermented vegetable product or a fermented cereal product comprising adding to the starting materials for fermentation a culture of Streptococcus macedonicus ACA-DC 198.

The invention further relates to a dairy product, a fermented meat product, a fermented vegetable product or a fermented cereal product obtainable by any of the methods of the invention for producing or storing a fermented product.

The invention also relates to a method for storing a non-fermented food product comprising adding to the product a co-culture or a protective culture or an adjunct culture of Streptococcus macedonicus ACA-DC 198.

The invention further relates to a non-fermented food product obtainable by any of the methods of the invention relating to non-fermented food products.

The invention, now being generally described, will be more readily understood by reference to the following examples, which are included merely for purposes of illustration of certain aspects and embodiments of the present invention and are not intended to limit the invention.

BRIEF DESCRIPTION OF THE FIGURES

FIG. 9. Purification of Streptococcus macedonicus ACA-DC 198 bacteriocin

TABLE 1

Inhibitory spectrum of macedocin

Figure 1:
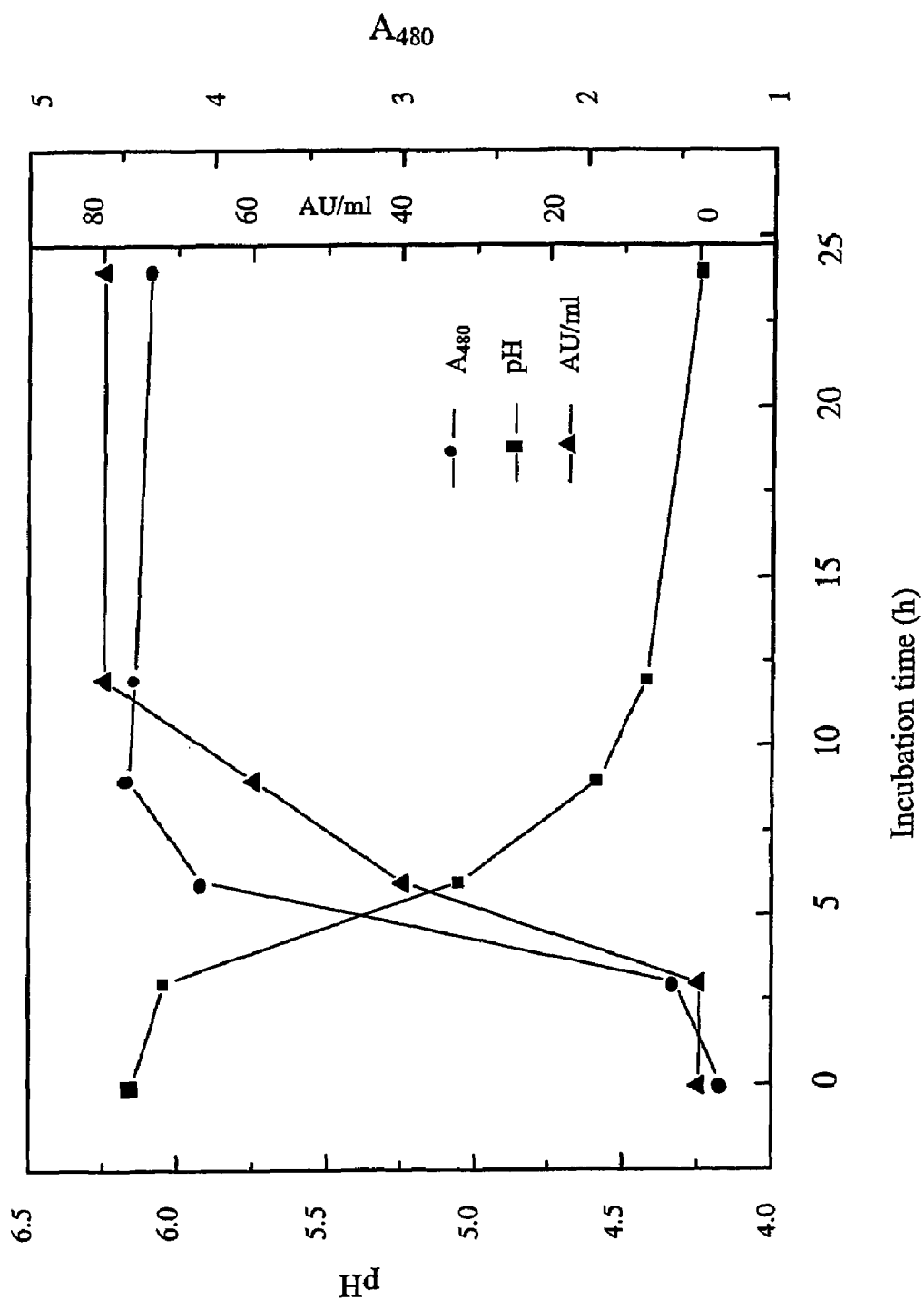
FIG. 1. Growth of S. macedonicus ACA-DC 198 and bacteriocin production in skim milk (10% wt/vol), containing 0.3% (wt/vol) yeast extract at 37° C.

| Indicator organism[c] | Cultivation medium[a], incubation temperature and aeration conditions | Sensitivity to macedocin[b] | |
|---|---|---|---|
| | | SUP[d] | ASP[e] |
| Bacillus cereus LMG 660 | BHI, 30° C., aerobic | − | +/− |
| Bacillus cereus LMG 6923[T] | BHI, 30° C., aerobic | − | − |
| Bacillus cereus LMG 13569 | BHI, 30° C., aerobic | − | + |
| Bacillus subtilis LMG 813 | BHI, 30° C., aerobic | − | + |
| Bacillus subtilis LMG 7135[T] | BHI, 30° C., aerobic | − | + |
| Bacillus subtilis LMG 17721 | BHI, 30° C., aerobic | + | + |
| Bacillus subtilis LMG 17722 | BHI, 30° C., aerobic | − | + |
| Bacillus subtilis LMG 17727 | BHI, 30° C., aerobic | +/− | + |
| Bacillus subtilis LMG 17728 | BHI, 30° C., aerobic | + | + |
| Bifidobacterium angulatum LMG 10503[T] | CAB, 37° C., anaerobic | − | + |
| Bifidobacterium bifidum LMG 13195 | CAB, 37° C., anaerobic | − | + |
| Bifidobacterium breve LMG 11042[T] | CAB, 37° C., anaerobic | +/− | + |
| Bifidobacterium breve LMG 13208 | CAB, 37° C., anaerobic | − | + |
| Bifidobacterium catenulatum LMG 11043 | CAB, 37° C., anaerobic | + | + |
| Bifidobacterium infantis LMG 8811[T] | CAB, 37° C., anaerobic | +/− | + |

TABLE 1-continued

Inhibitory spectrum of macedocin

| Indicator organism[c] | Cultivation medium[a], incubation temperature and aeration conditions | Sensitivity to macedocin[b] | |
|---|---|---|---|
| | | SUP[d] | ASP[e] |
| *Bifidobacterium infantis* LMG 10499 | CAB, 37° C., anaerobic | − | + |
| *Bifidobacterium longum* LMG 13197[T] | CAB, 37° C., anaerobic | +/− | + |
| *Bifidobacterium pseudolongum* subsp. *pseudolongum* LMG 11571[T] | CAB, 37° C., anaerobic | + | + |
| *Clostridium sporogenes* LMG 13570 | RCM, 37° C., anaerobic | − | + |
| *Clostridium tyrobutyricum* LMG 1285[T] | RCM, 37° C., anaerobic | + | + |
| *Clostridium tyrobutyricum* LMG 13571 | RCM, 37° C., anaerobic | − | + |
| *Enterococcus casseliflavus* EC 24 | MRS, 37° C., microaerophilic | − | − |
| *Enterococcus casseliflavus* LMG 10745[T] | MRS, 37° C., microaerophilic | +/− | + |
| *Enterococcus durans* LMG 10746[T] | MRS, 37° C., microaerophilic | − | + |
| *Enterococcus faecalis* LMG 7937[T] | MRS, 37° C., microaerophilic | − | − |
| *Enterococcus faecalis* LMG 16337 | MRS, 37° C., microaerophilic | − | +/− |
| *Enterococcus faecalis* Y | MRS, 37° C., microaerophilic | − | +/− |
| *Enterococcus faecium* CTC 492 | MRS, 37° C., microaerophilic | − | +/− |
| *Enterococcus faecium* LMG 11423[T] | MRS, 37° C., microaerophilic | +/− | +/− |
| *Enterococcus gallinarum* LMG 13129[T] | MRS, 37° C., microaerophilic | − | − |
| *Enterococcus hirae* LMG 6399[T] | MRS, 37° C., microaerophilic | − | − |
| *Lactobacillus acidophilus* ACA-DC 106 | MRS, 37° C., microaerophilic | − | − |
| *Lactobacillus acidophilus* LA$_1$ | MRS, 37° C., microaerophilic | − | + |
| *Lactobacillus acidophilus* LMG 13550[T] | MRS, 37° C., microaerophilic | − | + |
| *Lactobacillus brevis* ACA-DC 3407 | MRS, 37° C., microaerophilic | +/− | + |
| *Lactobacillus curvatus* subsp. *curvatus* LMG 13553[T] | MRS, 30° C., microaerophilic | + | + |
| *Lactobacillus delbrueckii* subsp. *bulgaricus* LMG 6901[T] | MRS, 37° C., microaerophilic | + | + |
| *Lactobacillus delbrueckii* subsp. *delbrueckii* ACA-DC 81 | MRS, 37° C., microaerophilic | + | + |
| *Lactobacillus fermentum* ACA-DC 114 | MRS, 37° C., microaerophilic | +/− | + |
| *Lactobacillus fermentum* LMG 6902[T] | MRS, 37° C., microaerophilic | + | + |
| *Lactobacillus fermentum* LMG 8896 | MRS, 37° C., microaerophilic | + | + |
| *Lactobacillus gasseri* ACA-DC 85a | MRS, 37° C., microaerophilic | + | + |
| *Lactobacillus helveticus* LMG 13555[T] | MRS, 42° C., microaerophilic | + | + |
| *Lactobacillus johnsonii* ATCC 33200 | MRS, 37° C., microaerophilic | +/− | + |
| *Lactobacillus paracasei* susbsp. *paracasei* ACA-DC 116 | MRS, 37° C., microaerophilic | − | − |
| *Lactobacillus paracasei* subsp. *paracasei* LMG 13552 | MRS, 37° C., microaerophilic | − | − |
| *Lactobacillus paracasei* susbsp. *tolerans* ACA-DC 177 | MRS, 37° C., microaerophilic | − | − |
| *Lactobacillus pentosus* ACA-DC 3356[T] | MRS, 37° C., microaerophilic | +/− | + |
| *Lactobacillus plantarum* ACA-DC 113 | MRS, 37° C., microaerophilic | + | + |
| *Lactobacillus plantarum* ACA-DC 142 | MRS, 37° C., microaerophilic | +/− | + |
| *Lactobacillus plantarum* ATCC 14917[T] | MRS, 37° C., microaerophilic | +/− | + |
| *Lactobacillus plantarum* LMG 13556 | MRS, 37° C., microaerophilic | − | + |
| *Lactobacillus rhamnosus* ACA-DC 112 | MRS, 37° C., microaerophilic | − | − |
| *Lactobacillus reuteri* ATCC 53608 | MRS, 37° C., microaerophilic | + | + |
| *Lactobacillus reuteri* LMG 13557[T] | MRS, 37° C., microaerophilic | + | + |
| *Lactobacillus sakei* subsp. *sakei* LMG 13558[T] | MRS, 30° C., microaerophilic | + | + |
| *Lactococcus garviae* ACA-DC 219 | MRS, 30° C., microaerophilic | +/− | + |
| *Lactococcus lactis* subsp. *cremoris* LMG 6897[T] | MRS, 30° C., microaerophilic | + | + |
| *Lactococcus lactis* subsp. *lactis* ACA-DC 46 | MRS, 30° C., microaerophilic | − | − |
| *Lactococcus lactis* subsp. *lactis* ACA-DC49 | MRS, 30° C., microaerophilic | − | − |
| *Lactococcus lactis* subsp. *lactis* ACA-DC 73 | MRS, 30° C., microaerophilic | − | − |
| *Lactococcus lactis* subsp. *lactis* LMG 6890[T] | MRS, 30° C., microaerophilic | + | + |
| *Lactococcus lactis* subsp. *lactis* LMG 8522 | MRS, 30° C., microaerophilic | + | + |
| *Leuconostoc mesenteroides* subsp. *cremoris* LMG 13562 | MRS, 25° C., microaerophilic | + | + |
| *Leuconostoc mesenteroides* subsp. *dextranicum* ACA-DC 135 | MRS, 25° C., microaerophilic | + | + |
| *Listeria innocua* CTC 1014 | BHI, 30° C., microaerophilic | − | + |
| *Listeria innocua* LMG 11387[T] | BHI, 30° C., microaerophilic | − | + |
| *Listeria innocua* LMG 13568 | BHI, 30° C., microaerophilic | − | + |
| *Listeria innocua* RZS | BHI, 30° C., microaerophilic | − | − |
| *Listeria ivanovii* LTH 3097 | BHI, 30° C., microaerophilic | − | + |
| *Listeria monocytogenes* Scott A | TSB, 30° C., microaerophilic | − | − |
| *Micrococcus luteus* LMG 4050T | NB, 30° C., aerobic | + | + |
| *Pediococcus pentosaceus* LMG 13560 | MRS, 30° C., microaerophilic | + | + |
| *Pediococcus pentosaceus* LMG 13561 | MRS, 30° C., microaerophilic | − | + |
| *Propionibacterium acidipropionici* LMG 13572 | MRS, 30° C., anaerobic | + | + |

TABLE 1-continued

Inhibitory spectrum of macedocin

| Indicator organism[c] | Cultivation medium[a], incubation temperature and aeration conditions | Sensitivity to macedocin[b] | |
|---|---|---|---|
| | | SUP[d] | ASP[e] |
| *Propionibacterium freudenreichii* subsp. *shermanii* LMG 16424[T] | MRS, 30° C., anaerobic | − | − |
| *Staphylococcus carnosus* LMG 13567 | BHI, 37° C., microaerophilic | +/− | + |
| *Streptococcus macedonicus* ACA-DC 198 | LAPTg, 37° C., microaerophilic | − | + |
| *Streptococcus macedonicus* ACA-DC 206[T] | MRS, 37° C., microaerophilic | − | − |
| *Streptococcus thermophilus* ACA-DC 4 | MRS, 42° C., microaerophilic | + | + |
| *Streptococcus thermophilus* ACA-DC 9 | MRS, 42° C., microaerophilic | + | + |
| *Streptococcus thermophilus* ACA-DC 79 | MRS, 42° C., microaerophilic | − | − |
| *Streptococcus thermophilus* LMG 13564 | MRS, 42° C., microaerophilic | + | + |
| *Streptococcus thermophilus* LMG 13565 | MRS, 42° C., microaerophilic | − | +/− |

[a]BHI: Brain Heart Infusion broth (Oxoid); MRS: de Man-Rogosa-Sharpe broth (Oxoid); RCM: Reinforced Clostridial Medium (Oxoid); NB: Nutrient Broth (Oxoid); TSB: Tryptone Soy Broth (Oxoid); CAB: Columbia Agar Base (contained special peptone (Oxoid) (23 g/l); glucose (Merck) (20 g/l), and sodium chloride (5 g/l); and was adjusted to pH 7.0 before autoclaving; LAPTg: see Example 1.
[b]'−' not sensitive (no inhibition zone), '+/−' weakly sensitive (hazy inhibition zone), '+' sensitive (clear inhibition zone)
[c]CTC: Centre de Tecnologia de la Carn, Monells, Spain; LMG: Laboratorium Microbiologie Gent, Gent, Belgium; RZS: Rijks Zuivel Station, Melle, Belgium; LTH: Lebensmittein Technologie Hohenheim, Hohenheim, Germany; ACA-DC: Collection of the Agricultural University of Athens, Greece; ATCC: American Type Culture Collection, Mansassas, USA.
[d]"SUP" refers to the inhibition assays performed with the cell free culture supernatant as described in Example 2.
[e]"ASP" refers to the inhibition assays performed with the cell free culture supernatant that was concentrated by ammonium sulfate precipitation as described in Example 2.

TABLE 2A

Bacteriocin production by *S. macedonicus* ACA-DC 198 in various growth media

| Growth medium | Bacteriocin[a] (AU/ml) |
|---|---|
| Skim milk (10%, wt/vol) | − |
| Skim milk (10%, wt/vol) supplemented with yeast extract (0.01%, wt/vol) | 100 |
| Skim milk (10%, wt/vol) supplemented with yeast extract (0.025%, wt/vol) | 200 |
| Skim milk (10%, wt/vol) supplemented with yeast extract (0.05%, wt/vol) | 300 |
| Skim milk (10%, wt/vol) supplemented with yeast extract (0.3%, wt/vol) | 200 |
| Skim milk (10%, wt/vol) supplemented with yeast extract (1.5%, wt/vol) | 300 |
| Skim milk (10%, wt/vol) supplemented with yeast extract (3.0%, wt/vol) | 300 |
| Skim milk (10%, wt/vol) supplemented with yeast extract (6.0%, wt/vol) | 200 |
| Skim milk (10%, wt/vol) supplemented with yeast extract (9.0%, wt/vol) | 400 |
| Skim milk (10%, wt/vol) supplemented with tryptone (0.3%, wt/vol) | 400 |
| Skim milk (10%, wt/vol) supplemented with tryptone (1.5%, wt/vol) | 400 |
| Skim milk (10%, wt/vol) supplemented with lactalbumin hydrolysate (0.3%, wt/vol) | 400 |
| Skim milk (10%, wt/vol) supplemented with lactalbumin hydrolysate (1.5%, wt/vol) | 400 |
| Skim milk (10%, wt/vol) supplemented with lactalbumin hydrolysate (3.0%, wt/vol) | 600 |
| Skim milk (10%, wt/vol) supplemented with lactalbumin hydrolysate (6.0%, wt/vol) | 600 |
| Skim milk (10%, wt/vol) supplemented with casamino acids (0.3%, wt/vol) | 150 |
| Skim milk (10%, wt/vol) supplemented with casamino acids (1.5%, wt/vol) | − |
| Skim milk (10%, wt/vol) supplemented with casein hydrolysate (0.3%, wt/vol) | 50 |
| Skim milk (10%, wt/vol) supplemented with casein hydrolysate (1.5%, wt/vol) | − |
| MRS broth | +/− |
| MRS broth, containing pepticase 2% (wt/vol) instead of polypeptone and meat extract | − |
| MRS broth, containing casein hydrolysate 2% (wt/vol) instead of polypeptone and meat extract | − |
| MRS broth, containing bacteriological peptone (0.75%, wt/vol), Lab Lemco (0.6%, wt/vol), yeast extract (0.3%, wt/vol) | − |
| MRS broth, containing bacteriological peptone (0.5%, wt/vol), Lab Lemco (0.4%, wt/vol), yeast extract (0.2%, wt/vol) | − |
| MRS broth containing bacteriological peptone (0.25%, wt/vol), Lab Lemco (0.2%, wt/vol), yeast extract (0.1%, wt/vol) | − |
| MRS broth, supplemented with lactose 2% | − |
| MRS broth, supplemented with whey protein concentrate 1 or 2% (wt/vol) | − |
| MRS broth, supplemented with lactose 2% and whey protein concentrate 1 or 2% (wt/vol) | − |
| MRS broth, supplemented with lactose 2% and lactalbumin hydrolysate 2% (wt/vol) | − |
| MRS broth, supplemented with 1% (v/v) peptonised milk | − |
| MRS broth, supplemented with 5% (v/v) peptonised milk | − |
| MRS broth, supplemented with 10% (v/v) peptonised milk | − |
| MRS broth, supplemented with 20% (v/v) peptonised milk | − |
| MRS broth, supplemented with 1% (v/v) skimmed milk | − |
| MRS broth, supplemented with 5% (v/v) skimmed milk | − |
| MRS broth, supplemented with 10% (v/v) skimmed milk | − |
| MRS broth, supplemented with 20% (v/v) skimmed milk | − |

TABLE 2A-continued

Bacteriocin production by *S. macedonicus* ACA-DC 198 in various growth media

| Growth medium | Bacteriocin[a] (AU/ml) |
|---|---|
| **MRS (L + P), supplemented with 2% glucose | − |
| **MRS (T), supplemented with 2% glucose | − |
| **MRS (LH), supplemented with 2% glucose | − |
| **MRS (L + P), supplemented with 4% glucose | − |
| **MRS (T), supplemented with 4% glucose | − |
| **MRS (LH), supplemented with 4% glucose | − |
| **MRS (L + P), supplemented with 2% lactose | − |
| **MRS (T), supplemented with 2% lactose | − |
| **MRS (LH), supplemented with 2% lactose | − |
| **MRS (L + P), supplemented with 4% lactose | − |
| **MRS (T), supplemented with 4% lactose | − |
| **MRS (LH), supplemented with 4% lactose | − |

[a] '−' no bacteriocin production, '+/−' occasional and weak bacteriocin production; *Lb. sakei* subsp. *sakei* LMG 13558$^T$ was used as indicator strain.
**In these comparative experiments, Lab-Lemco powder (L) and bacteriological peptone (P) in MRS broth are replaced by tryptone (T) or lactalbuminhydrolysate (LH) (1.8% (w/v). Skim milk: Belgomilk, Kallo, Belgium; yeast extract: Merck (Darmstadt, Germany); casamino acids: Bio-Trading (Bierbeek, Belgium); lactalbumin hydrolysate, casein hydrolysate, tryptone, bacteriological peptone, and Lab Lemco: Oxoid (Basingstoke, Hampshire, England); MRS broth: Oxoid, Merck, Biokar Diagnostics (Beauvais, France), and LabM (Bury, England); pepticase: Sigma (Steinheim, Germany); lactose: Merck; whey protein concentrate: supplier (Danmark Protein, Denmark); M17 broth, Elliker broth and Nutrient broth: Biokar Diagnostics.

TABLE 2B

Bacteriocin production in various milk media supplemented with 0.3% yeast extract (wt/vol).

| Growth medium | Bacteriocin[a] (AU/ml) |
|---|---|
| Full cream milk (fresh) | 300 |
| Semi-skimmed milk (fresh) | 200 |
| Skimmed milk (fresh) | 200 |
| Skim milk (10%, wt/vol) (derived from milk powder) | 200 |

TABLE 3

Fermented foods and beverages and their associated microorganisms

| Type of fermented product | Examples | Associated microorganisms |
|---|---|---|
| dairy products | yoghurt, butter, milk, buttermilk, cheese, kefir | lactic acid bacteria, propionibacteria, brevibacteria, micrococci, yeasts, moulds |
| fermented meats | fermented sausage | lactic acid bacteria, catalase-positive cocci (micrococci, staphylococci), moulds, yeasts |
| fermented fish products | fish paste, fish sauce | lactic acid bacteria |
| fermented vegetables | olives, sauerkraut, pickles, cucumbers | lactic acid bacteria |
| fermented cereals | bread, sourdough, crackers | yeast, lactic acid bacteria |
| oriental fermented foods | soy sauce | lactic acid bacteria, moulds, yeast |
| alcoholic beverages | beer, wine, cider, sake, distillates | yeast, lactic acid bacteria |
| stimulants | coffee, cocoa, tea | lactic acid bacteria, acetic acid bacteria |
| vinegar | wine vinegar | acetic acid bacteria |

TABLE 4

Fermented foods and beverages and their associated lactic acid bacteria

| Type of fermented product | Lactid acid bacteria* |
|---|---|
| dairy products | |
| hard cheeses without eyes | *L. lactis* subsp. *lactis*, *L. lactis* subsp. *cremoris* |
| cheeses with small eyes | *L. lactis* subsp. *lactis*, *L. lactis* subsp. *lactis* var. *diacetylactis*, *L. lactis* subsp. *cremoris*, *Leuc. mesenteroides* subsp. *cremoris* |
| Swiss cheese | *Lb. delbrueckii* subsp. *lactis*, *Lb. helveticus* |
| butter and buttermilk | *L. lactis* subsp. *lactis*, *L. lactis* subsp. *lactis* var. *diacetylactis*, *L. lactis* subsp. *cremoris*, *Leuc. mesenteroides* subsp. *cremoris* |
| yoghurt | *Lb. delbrueckii* subsp. *bulgaricus*, *S. thermophilus* |
| fermented, probiotic milk | *Lb. casei*, *Lb. acidophilus*, *Lb. johnsonii*, *B. animalis*, *B. lactis*, *B. bifidum*, *B. longum* |
| kefir | *Lb. kefir*, *Lb. kefiranofacies*, *Lb. brevis* |

TABLE 4-continued

Fermented foods and beverages and their associated lactic acid bacteria

| Type of fermented product | Lactid acid bacteria* |
|---|---|
| fermented meats | |
| fermented sausage (Europe) | Lb. sakei, Lb. curvatus, Lb. plantarum, Lb. jensenii |
| fermented sausage (USA) | P. acidilactici, P. pentosaceus |
| fermented fish products | Lb. alimentarius, C. piscicola |
| fermented vegetables | |
| sauerkraut | Leuc. mesenteroides, Lb. plantarum, P. acidilactici |
| pickles | Leuc. mesenteroides, P. cerevisiae, Lb. brevis, Lb. plantarum |
| fermented olives | Leuc. mesenteroides, Lb. pentosus, Lb. plantarum |
| fermented vegetables | P. acidilactici, P. pentosaceus, Lb. plantarum, Lb. fermentum |
| soy sauce | T. halophilus |
| fermented cereals | |
| sour dough | Lb. sanfransiscensis, Lb. farciminis, Lb. fermentum, Lb. brevis, Lb. plantarum, Lb. amylovorus, Lb. reuteri, Lb. pontis, Lb. panis, Lb. cerealis, Lb. frumenti, Lb. paralimentarius, W. cibaria |
| alcoholic beverages | |
| wine (malolactic fermentation) | O. oeni |
| rice wine | Lb. sakei |

*B. = Bifidobacterium, C. = Carnobacterium, L. = Lactococcus, Lb. = Lactobacillus, Leuc. = Leuconostoc, O. = Oenococcus, P. = Pediococcus, S. = Streptococcus, T. = Tetragenococcus, W. = Weissella

EXAMPLES

Example 1

Materials and Methods

Strain and Growth Conditions.

S. macedonicus ACA-DC 198, a strain isolated from Greek Kasseri cheese, was obtained from the ACA-DC Collection of the Laboratory of Dairy Research at the Agricultural University of Athens, Athens, Greece. It was stored at −30° C. in sterile skim milk (10%, wt/vol; Irish Dairy Bord, Dublin, Ireland). Before experimental use, the strain was subcultured twice (inoculum of 1%, vol/vol) in sterile milk, containing yeast extract (0.3%, wt/vol; Merck, Darmstadt, Germany), at 37° C. for 24 h, unless stated otherwise, to obtain fresh cultures. Final growth was performed in the latter medium under the same conditions. Growth was assessed by measurement of the pH and the optical density at 480 nm (Kanasaki et al. 1975). Sterilisation was performed by autoclaving (2.1 atm) at 121° C. for 20 min.

Protein Determination

Protein concentrations were determined according to the method of Lowry et al. (1951) with bovine serum albumin as a standard.

Quantitavive Determination of Bacteriocin Activity

Two methods were used for the determination of bacteriocin activity, the well diffusion assay and the soft agar assay (De Vuyst et al. 1996).

The well diffusion assay was applied in the macedocin purification and biochemical characterization procedure (using Lactococcus lactis subsp. lactis LMG 6890$^T$ as indicator strain), as well as for testing bacteriocin activity against Clostridium strains. Briefly, 15 ml of M17 agar (Oxoid, Basingstoke, Hampshire, England), containing 450 μl of a fresh culture of Lactococcus lactis subsp. lactis LMG 6890$^T$, were poured into a Petridish, and wells of 5 mm diameter were made in the solidified medium. The wells were filled with 50 μl of serial twofold dilutions in 50 mM sodium phosphate buffer, pH 6.5, of the bacteriocin sample, and inhibition zones were perceived after 12 h of incubation at 30° C. The activity was expressed in arbitrary units (AU) per ml, corresponding to 50 μl of the highest dilution causing a clear zone of inhibition. The method was performed similarly with Clostridium strains, except that RCM agar (Oxoid) was used, and that 25 μl of the sample was added to the wells.

The soft agar assay was applied for determining the antimicrobial spectrum (apart from Clostridium strains) of the bacteriocin. Briefly, 10 μl of serial twofold dilutions in 50 mM sodium phosphate buffer, pH 6.5, of the S. macedonicus ACA-DC 198 cell-free culture supernatant as such, or after ammonium sulfate precipitation (50% saturation), were spotted onto lawns of the indicator organism. These lawns were prepared by propagating fresh indicator cultures to an optical density at 600 nm of 0.45, and adding 100 μl of the cell suspension to 3.5 ml of overlay agar. Overlaid agar plates were incubated for at least 12 h and examined for inhibition zones. The activity was expressed in arbitrary units (AU) per ml, corresponding to 10 μl of the highest dilution causing a clear zone of inhibition.

Example 2

Inhibitory Spectrum and Mode of Inhibition

Strains and Methods

The bacterial strains used as indicator organisms and their growth conditions are listed in Table 1. The antagonistic activity of S. macedonicus ACA-DC 198 was tested by the soft agar assay or the well diffusion assay (Clostridium strains) as described above, except that only cell-free culture supernatant and the fraction obtained through ammonium sulfate precipitation (50% saturatation) were tested (no dilutions made). For each indicator strain the respective solid medium was used. Solid media were prepared by adding 1.5% (wt/vol) of granulated agar (Oxoid) to the respective broth media. Overlay agar was prepared by the addition of 0.75% (wt/vol) of granulated agar (Oxoid).

To investigate its mode of inhibition, partially purified bacteriocin was obtained according to the two-step procedure of De Vuyst et al. (1996) except that 500 ml of skim milk (10%, wt/vol) containing yeast extract (0.3%, wt/vol), inoculated with S. macedonicus ACA-DC 198 and incubated at 37° C. for 12 h (inoculum of 1%, wt/vol), was used. Also, isopropanol was used instead of a mixture of chloroform and methanol. The inhibition assay was as follows: Two ml or four ml of a bacteriocin solution containing 3200 AU/ml was added to 9 ml of an exponentially growing culture of Lb. sakei subsp. sakei LMG 13558$^T$ (the most sensitive strain), Lb. paracasei subsp. paracasei LMG 13552 (an insensitive strain), and S. macedonicus ACA-DC 198 (the producer strain) in the Man-Rogosa-Sharpe (MRS) medium (De Man, et al. 1960). Incubations took place at 30, 30, and 37° C., respectively. Growth was followed by measuring the optical density at 600 nm, and by plate counting on LAPTg (S. macedonicus; Raibaud et al., 1961) and MRS (lactobacilli; Oxoid) agar. LAPTg agar was composed of yeast extract (Merck) (10 g/l), bacteriological peptone (Oxoid) (15 g/l), tryptone (Oxoid) (10 g/l), Tween 80 (Merck) (1 m/l), glucose (Merck) (10 g/l), and granulated agar (Oxoid) (15 g/l). All media were sterilized in an autoclave at 121° C. and 2.1 bar for 20 min; glucose was sterilized separately.

For the producer strain S. macedonicus ACA-DC 198, the inhibition assay was also performed in a medium that favors bacteriocin production, namely skimmed milk supplemented with yeast extract (0.3%, wt/vol). Two ml of a bacteriocin solution, containing 1,600 AU/ml, were added to 5 ml of an exponentially growing culture. The culture was incubated at 37° C. and growth was followed by measuring the optical density at 480 nm (Kanasaki et al., 1975), and by plate counting on LAPTg (Raibaud et al., 1961). For the control strain, 2 ml of a milk protein solution was added instead of 2 ml of the bacteriocin solution. The milk protein solution was prepared by applying the two-step isolation method (De Vuyst et al., 1996) on 500 ml sterilized skimmed milk supplemented with yeast extract (0.3%, wt/vol). Briefly, the caseins were removed by adjusting the pH of the milk to 4.0 with lactic acid (90%) at 55° C. followed by centrifugation (20,000 g, 30 min, 4° C.). After salting out with ammonium sulfate (50% saturation), the whey proteins were collected by centrifugation (20,000 g, 30 min, 4° C.) and dissolved in sodium phosphate buffer (pH 6.5). Finally, this whey fraction was subjected to an isopropanol extraction, the sediment was dissolved in ultra pure water and 2 ml were added to the control culture.

Results

Inhibitory Spectrum of the Macedocin

The macedocin exhibited a broad inhibitory spectrum (Table 1). When the cell free culture supernatant of S. macedonicus ACA-DC 198 was tested against the 84 indicator strains, 41 of them were found sensitive. The activity spectrum included several lactic acid bacteria, as well as Gram-positive spoilage and pathogenic bacteria such as Bacillus subtilis and Clostridium tyrobutyricum. Apart from Enterococcus casseliflavus LMG 10745$^T$ and Enterococcus faecium 11423$^T$, all enterococci strains tested were not affected. This was also the case with the Listeria monocytogenes, Listeria innocua and Listeria ivanovii strains used. These data are represented in Table 1 in the column with notation "SUP".

When the S. macedonicus ACA-DC 198 cell free culture supernatant was concentrated by ammonium sulfate precipitation, and then tested against the same set of indicator strains, more strains (Walstra et al. 1993) were found sensitive. With this preparation, activity was moreover detected against Bacillus cereus, Clostridium sporogenes, Listeria innocua and Listeria ivanovii. Even the producer strain itself was inhibited then. These data are represented in Table 1 in the column with notation "ASP".

A quantitative screening was performed for strains clearly inhibited by the cell-free culture supernatant (data not shown). The highest inhibition was observed with L. lactis subsp. lactis LMG 6890$^T$ (150 AU/ml), Lb. sakei subsp. sakei LMG 13558$^T$ (spot-on-lawn method: 225 AU/ml), Micrococcus luteus LMG 4050T (200 AU/ml) Cl. tyrobutyricum LMG 1285$^T$ (120 AU/ml) and Propionibacterium acidipropionici LMG 13572 (250 AU/ml). Using the well-diffusion method, Cl. tyrobutyricum LMG 1285$^T$ and Lb. sakei subsp. sakei LMG 13558$^T$ showed the same sensitivity (120 and 160 AU/ml, respectively).

Mode of Inhibition

Figure 2:
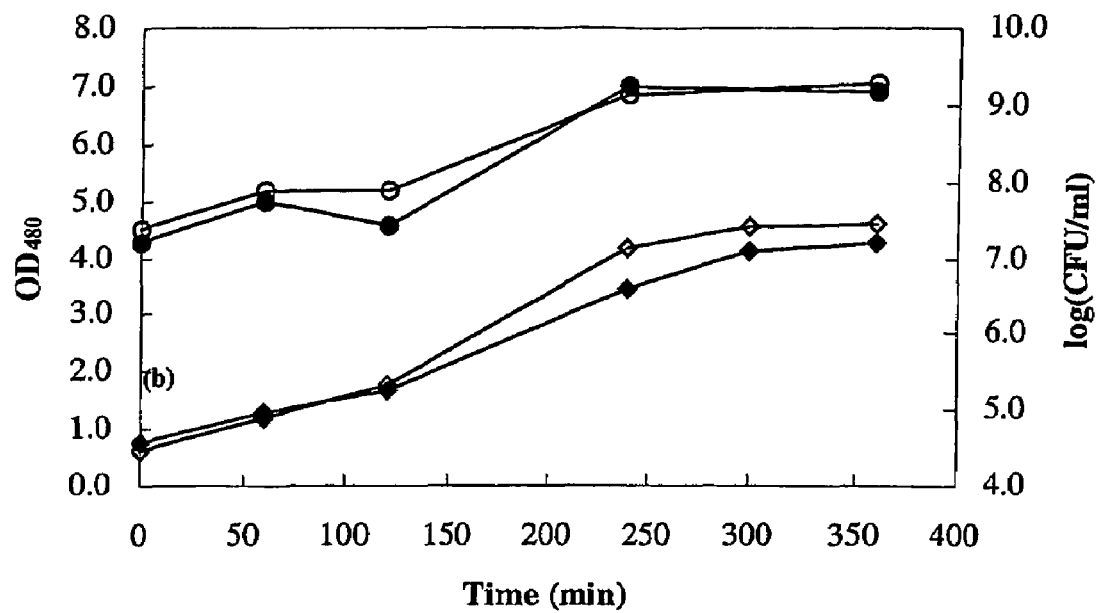
FIG. 2: Mode of action of macedocin against (a) S. macedonicus ACA-DC 198 grown in skimmed milk supplemented with yeast extract (0.3%, wt/vol); (b) S. macedonicus grown in MRS broth; (c) Lb. sakei subsp. sakei LMG 13558$^T$ grown in MRS and (d) Lb. paracasei subsp. paracasei LMG 13552 grown in MRS; ○, ●, log (CFU/ml); ◆, ◇, $OD_{600}$ (MRS) or $OD_{480}$ (milk medium); ●, ◆, with addition of bacteriocin (400 AU/ml in MRS or 600 AU/ml in milk medium); ○, ◇, without bacteriocin.
Figure 2:
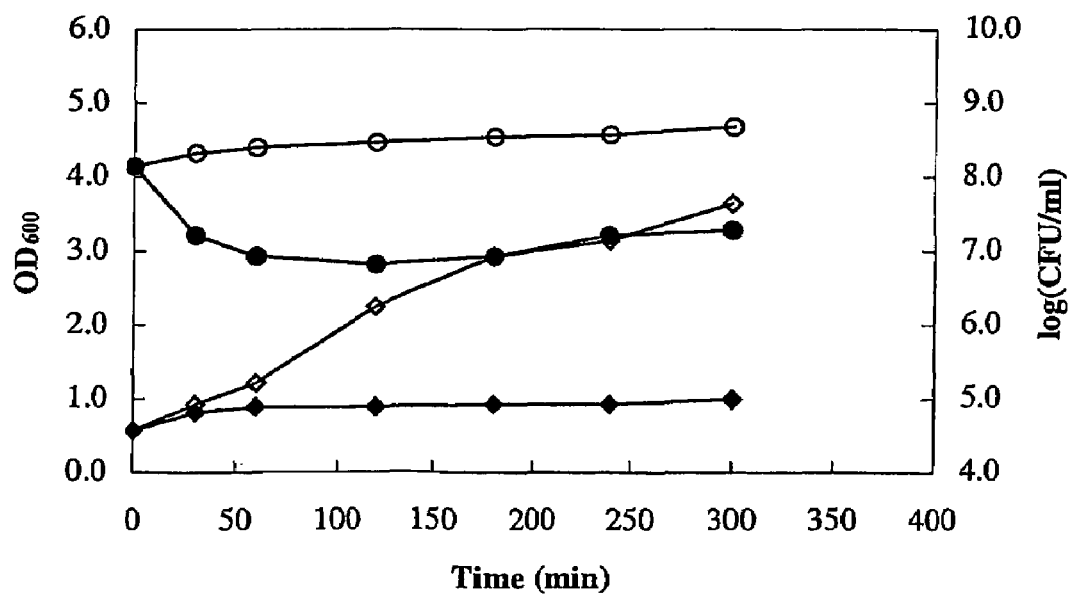

Exposure of the indicator strain Lb. sakei subsp. sakei LMG 13558$^T$ to partially purified bacteriocin (400 AU/ml) resulted in a small (less than one log unit) reduction in viable cell count, namely from $1.9 \times 10^8$ to $5.5 \times 10^7$ CFU/ml after 5 h of incubation at 30° C. (FIG. 2c). Increasing the bacteriocin activity (to 800 AU/ml) did not result in a higher reduction of the indicator cell count. The initial population of $2.3 \times 10^8$ CFU/ml ($OD_{600}$=0.71) was reduced to $1.3 \times 10^8$ CFU/ml after 1 h ($OD_{600}$=0.77), while a population level of $4.2 \times 10^7$ CFU/ml ($OD_{600}$=0.86) was reached at the end of the incubation period. Under these experimental conditions, the bacteriocin exhibited a bactericidal mode of action.

The addition of macedocin did not influence the growth of Lb. paracasei subsp. paracasei LMG 13552 (FIG. 2d). After 5 h of incubation the viable cell count was increased from $1.2 \times 10^8$ CFU/ml to $6.1 \times 10^8$ CFU/ml for the control strain, while in the presence of the bacteriocin, the cell count increased from $1.4 \times 10^8$ CFU/ml to $5.7 \times 10^8$ CFU/ml. The optical density (at 600 nm) of the cell suspensions increased by 2.2 and 2.3 absorbancy units for the control and the treated cell suspensions, respectively.

When the producer strain was grown in MRS in the presence of partially purified bacterlocin (400 AU/ml), a tenfold reduction of the viable cell count, from $1.4 \times 10^8$ to $8.4 \times 10^8$ CFU/ml, was observed after 1 h of incubation at 37° C. (FIG. 2b). Incubation for more than 1 h did not significantly change the number of viable cells of S. macedonicus ACA-DC 198. After 5 h of incubation the population level reached $1.9 \times 10^7$ CFU/ml, indicating a slight re-growth of the producer strain. A similar effect was obtained with a bacteriocin activity of 800 AU/ml except that no re-growth phase was observed. The S. macedonicus population was reduced from $1.2 \times 10^7$ to $7.5 \times 10^5$ CFU/ml in 1 h ($OD_{600}$=0.86), remained almost constant during further incubation, and reached a population level of $4.0 \times 10^5$ CFU/ml after 5 h ($OD_{600}$=0.85). Under these conditions, the producer strain clearly displayed auto-inhibition. This cannot be attributed to the presence of other end products such as lactic acid. At the beginning and the end of the incubation period, the cell-free culture supernatant of the control strain was assayed for antimicrobial activity against S. macedonicus ACA-DC 198 as indicator strain. No inhibition zones were observed, indicating that the growth inhibition was due to the presence of the macedocin. The absorbance values of all treated cell suspensions remained constant during incubation in the presence of bacteriocin, indicating the absence of cell lysis.

When S. macedonicus ACA-DC 198 was grown in the bacteriocin production favorable medium (skimmed milk supplemented with yeast extract) and in the presence of partially purified bacteriocin (600 AU/ml) no auto-inhibition was observed. The control strain as well as the strain in the presence of the macedocin reached the stationary phase after 6 h of incubation (FIG. 2a). At that moment, the optical density of the control suspension and the experimental suspension was 4.6 and 4.3 absorbance units, respectively, while the viable cell count reached $1.9 \times 10^9$ CFU/ml and $1.5 \times 10^9$ CFU/ml, respectively. In the inhibition assay, the bacteriocin activity (600 AU/ml) remained constant during the incubation period. For the control strain, no bacteriocin activity was determined at the beginning of the experiment, while an activity of 200 AU/ml was observed after 12 h of incubation.

Investigation of the effect of macedocin on the optical density of actively metabolizing cells of the susceptible indicator strain *Lb. sakei* subsp. *sakei* LMG $13558^T$ at 30° C. indicated that, in spite a slight decrease in the number of CFU, there was no apparent change in the optical density of the culture, and hence, that the lethal effect was not accompanied by cell lysis. In this context, the activity of macedocin against the indicator strain *Lb. sakei* subsp. *sakei* LMG $13558^T$ can be considered bacteriocidal. Tagg et al. (1973) observed a similar reduction in viable cell counts when streptocin A was added to resting cells suspensions of Group A *streptococcus* strain PF 1643 incubated at 25 and 37° C., while the cell death induced was not associated with cell lysis. In that case, temperature of incubation had a marked effect on the bacteriocidal action, with less killing at lower temperature.

Although specific immunity proteins and a secondary ABC-transporter system are assumed to protect the producer strain against the inhibitory action of its own product (McAufiffe et al., 2001), auto-inhibition of *S. macedonicus* ACA-DC 198 was noticed when the strain was grown in MRS broth, in which *S. macedonicus* ACA-DC 198 is actually not able to produce macedocin. On the contrary, when the producer stain was grown in milk supplemented with yeast extract, a medium that favors macedocin production, no auto-inhibition was observed.

Example 3

Purification and Characterization of the *Streptococcus macedonicus* Bacteriocin Purification All the purification steps were performed at room temperature, using an FPLC system of Waters (WATERS™ 650E Advanced Protein Purification System). All columns used were purchased from Pharmacia-LKB (Uppsala, Sweden).

A combination of ammonium sulfate precipitation, anion- and cation-exchange chromatography, reverse-phase chromatography, and gel filtration has been applied for the purification of the bacteriocin to homogeneity as follows:

Skim milk (500 ml), supplemented with yeast extract (0.3%, wt/vol.), was inoculated with *S. macedonicus* ACA-DC 198 (inoculum of 1%, vol./vol.), and incubated at 37° C. for 24 h. The cells were removed by centrifugation at 15 000 g at 4° C. for 30 min. The supernatant was adjusted to pH 6.5 by 5 N NaOH, and saturated up to 50% with $(NH_4)_2SO_4$. After overnight stirring at 4° C., the bacteriocin was pelleted by centrifugation at 15 000 g at 4° C. for 30 min, and dissolved in 20 mM Tris buffer, pH 7.5.

The sample was then applied on a Resource Q column (16 mm i.d.×30 mm), equilibrated with 20 mM Tris-HCl buffer, pH 7.5. Elution was performed at a flow rate of 2 ml/min, with a linear gradient of 0-1.0 M NaCl in the same buffer. The non-retained, bacteriocin-containing fraction was properly diluted in 20 mM phosphate buffer, pH 5.5, and applied on a Resource S column (16 mm i.d.×30 mm), equilibrated with the same buffer. Elution was performed at a flow rate of 2 ml/min, with a linear gradient of 0-1.5 M NaCl in the same buffer. The bacteriocin-containing fractions were pooled, properly diluted in double distilled water ($ddH_2O$), containing 0.1% (vol./vol.) trifluoroacetic acid (TFA), and applied on a Resource RPC column (6.4 mm i.d×100 mm), equilibrated with the same solvent. Elution was performed at a flow rate of 2 m/min, with a linear gradient of 0-100% acetonitrile, containing 0.1% (vol./vol.) TFA. The bacteriocin-containing fractions were pooled, lyophylised and dissolved in 20 mM phosphate buffer, pH 6.0, containing 0.25 M NaCl. The sample was then filtered on a Superdex Peptide HR 10/30 column, equilibrated with the same buffer. Elution was performed at a flow rate of 0.5 ml/min. The bacteriocin was eluted as a symmetrical peak. The bacteriocin-containing fractions were pooled and used for the characterization of the bacteriocin.

The recovery and degree of purification are summarized in FIG. 9.

Molecular Weight Determination

PAGE

Two electrophoretic systems were applied to control the purification steps and to determine the molecular weight of the bacteriocin. SDS-PAGE (10% acrylamide separating gel, in the presence of sodium dodecyl sulphate (SDS) and β-mercaptoethanol) was performed according to Laemmli (1970). Myosin (205.000), β-galactosidase (116.000), phosphorylase b (97.400), bovine serum albumin (66.000), egg albumin (45.000) and carbonic anhydrase (29.000) were used as marker proteins (Sigma, Steinheim, Germany). Discontinuous tricine-SDS-PAGE (Disc-PAGE) (3.84, 9.6 and 20% acrylamide for the stacking, spacer and separating gel, respectively, and in the presence of SDS and β-mercaptoethanol) was performed according to the procedure of Schäagger and von Jagow (1987). Cytochrome c (12 500), aprotinin (6 500) and substance P (1348) were used as marker proteins (Sigma).

The latter system was used for the post-electrophoretic detection of bacteriocin activity. After electrophoresis at a constant voltage of 30 V for 1 h followed by 90 V for 11 h, the gel was cut into two parts. The part containing the molecular weight marker was stained for 1 h. This part of the gel was then destained during 2 h and washed overnight with distilled water. The staining and destaining solution contained 50% (vol/vol) methanol and 0.7% (vol/vol.) acetic acid, with and without 0.2% Coomassie Brilliant Blue R-250 (Sigma), respectively. The other part of the gel was assayed for antimicrobial activity. This part was washed with ultrapure water for 7 h, overlaid with soft MRS agar (0.7%), inoculated with the indicator strain *Lb. sakei* subsp. *sakei* LMG $13558^T$ (inoculum of 4%, vol/vol), incubated at 30° C. for 24 h, and observed for the formation of inhibition zones.

Figure 3:
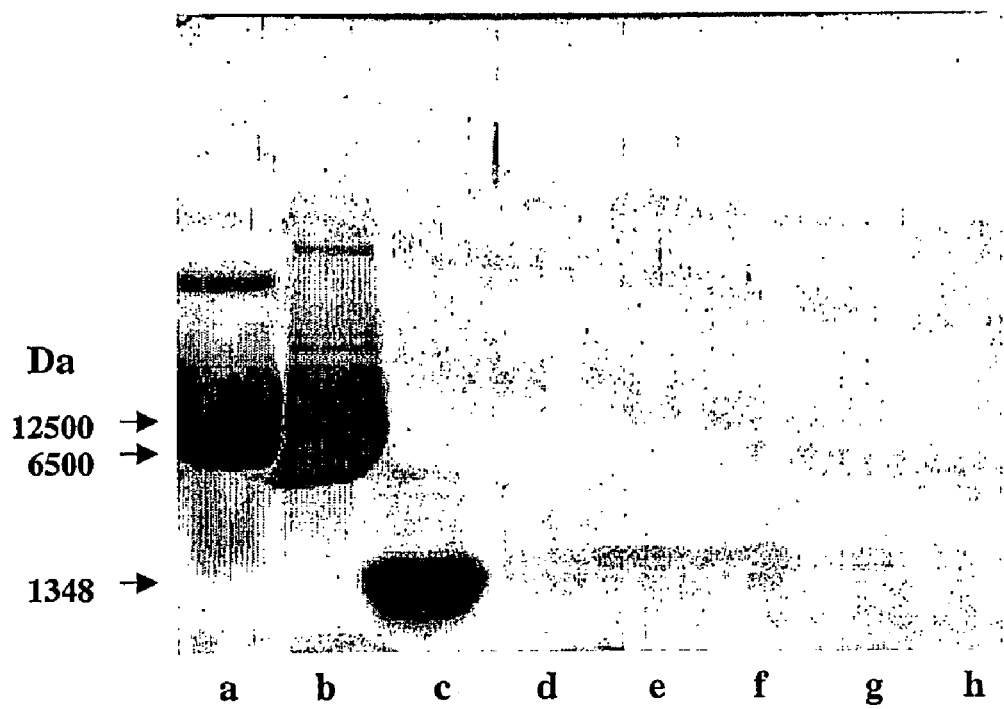
FIG. 3. (a) Tricine SDS-PAGE. Lanes: a, b and c, marker proteins (cytochrome C, aprotinin and substance P. respectively); d, e, f, g and h; active fractions from the Superdex Peptide HR 10/30 column (fractions 34, 35, 36, 37 and 38 respectively). (b) Post-electrophoretic detection of the antimicrobial activity towards Lb. sakei subsp. sakei LMG 13558$^T$ as indicator strain.
Figure 3:
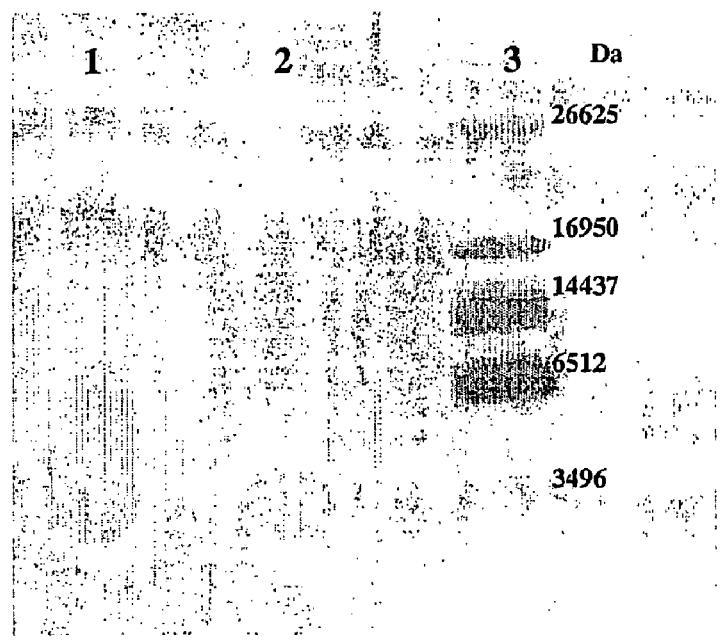

In the discontinuous tricine-SDS-PAGE analysis the purified bacteriocin gave only one band, which corresponded to a molecular weight of approximately 2,500 (FIG. 3a). In the post-electrophoretic detection, this band was active against the indicator strain *Lb. sakei* subsp. *sakei* LMG $13558^T$ (FIG. 3b). By gel filtration chromatography on the Superdex Peptide HR 10/30 column, previously standardized with cytochrome c (12, 500), aprotinin (6, 500), and substance P (1, 348), a molecular weight of 550 was calculated.

Mass Spectrometry

Mass spectra were recorded on both a MALDI-TOF mass spectrometer (Micromass, Manchester, UK) for mass determination of the intact polypeptide, and on a Q-TOF mass spectrometer equipped with a nano-electrospray source for MS/MS-experiments. For MALDI-TOF MS, 1 µl of the HPLC fractions were mixed with a 50 mM α-cyanohydroxy cinnamic acid matrix and spotted on the MALDI-target plate where it was allowed to dry by air. For electrospray analysis, 3 µl of a HPLC fraction were mixed with a similar amount of 50% acetonitrile/0.1% formic acid in water, and this mixture was loaded on a nanospray capillary (Protana, Odense, Denmark). Generally, 1250 V was applied on the spraying capillary, which was gently broken to initiate the spray formation. Argon was used as CID-gas for MS/MS experiments at a 1 bar pressure. The collision energy was set at 40 V.

Figure 4:
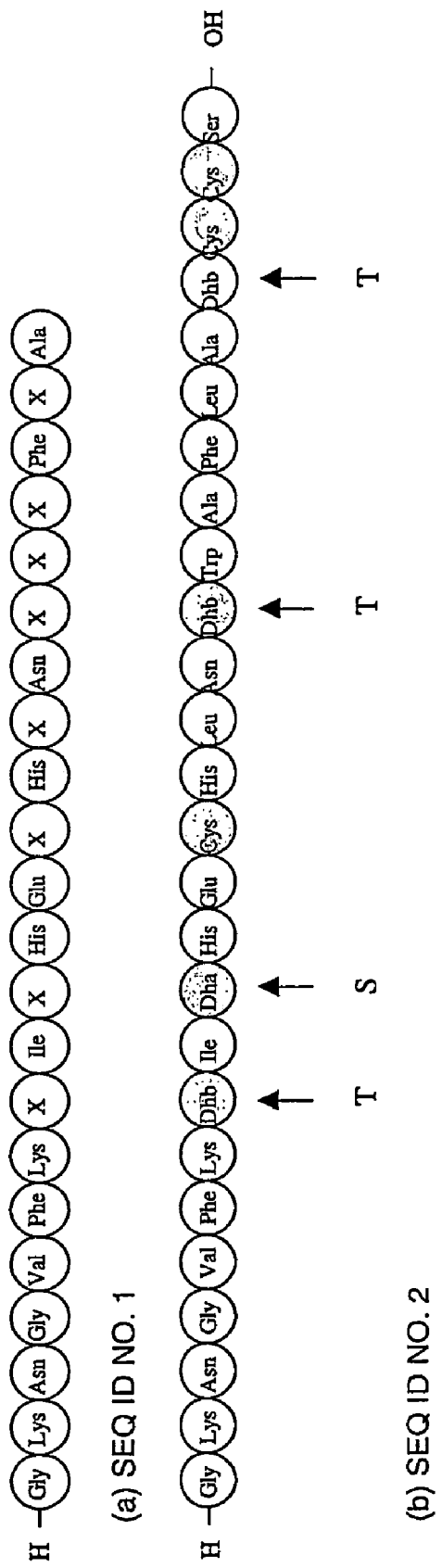
FIG. 4. (a) The amino acid sequence of the Streptococcus macedonicus ACA-DC 198 bacteriocin (SEQ ID NO 1) and (b) of SA-FF22 from Streptococcus pyogenes FF22 (SEQ ID NO 2) (Jack et al. 1994). Shaded residues are cross-linked through thioether bonds to form lanthionine (didehydroalanine and Cys) and methyllanthionine (didehydrobutyrine and Cys). T, Threonine; S, Serine; Dha, Didehydroalanine; Dhb, Didehydrobutyrine.
Figure 5:
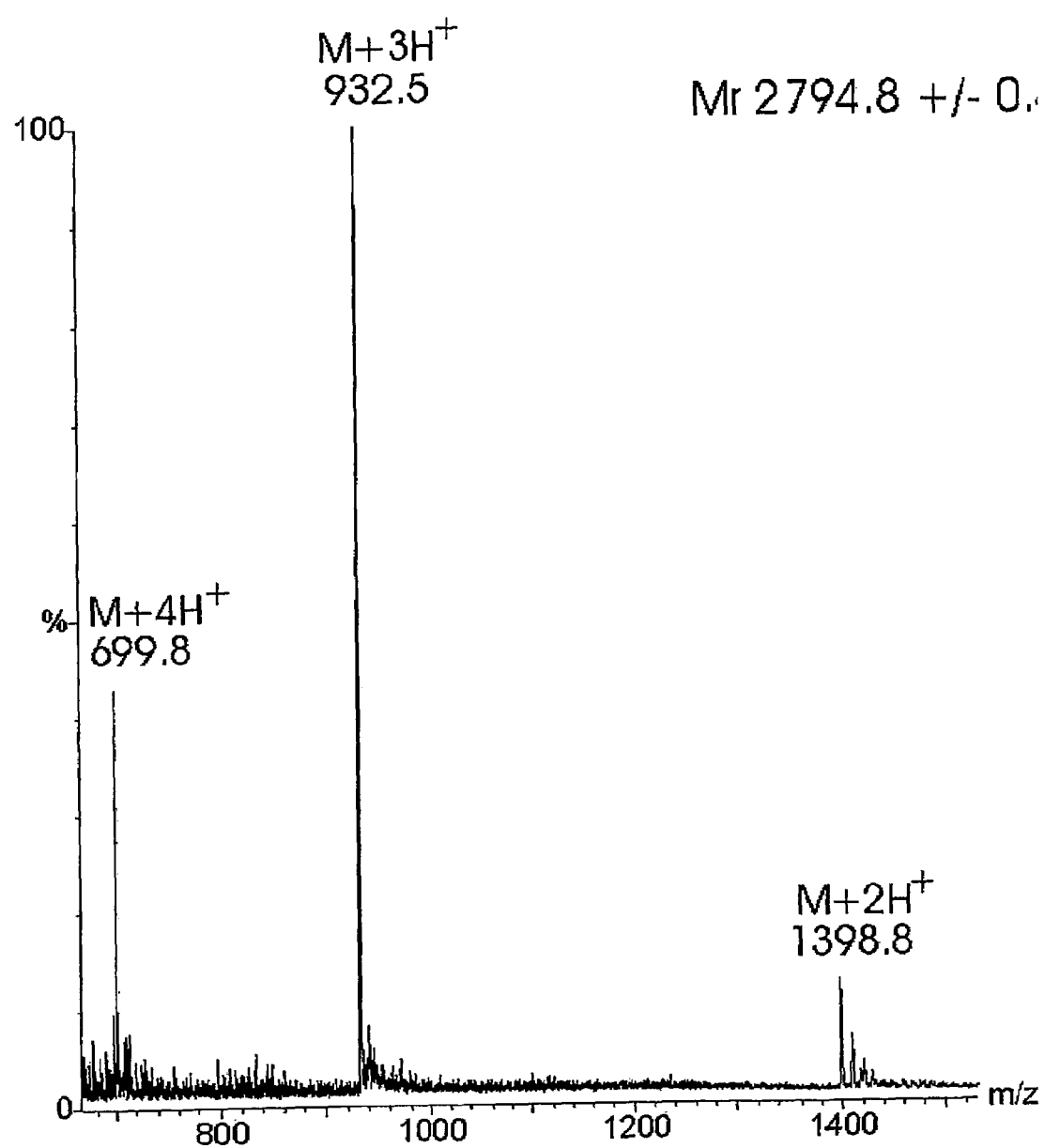
FIG. 5. Electron spray ionization mass spectrometry analysis of Streptococcus macedonicus ACA-DC 198 bacteriocin. The recorded multiple charged ions are consistent with a molecular mass estimate of 2 794.76±0.42 Da.
Figure 6A:
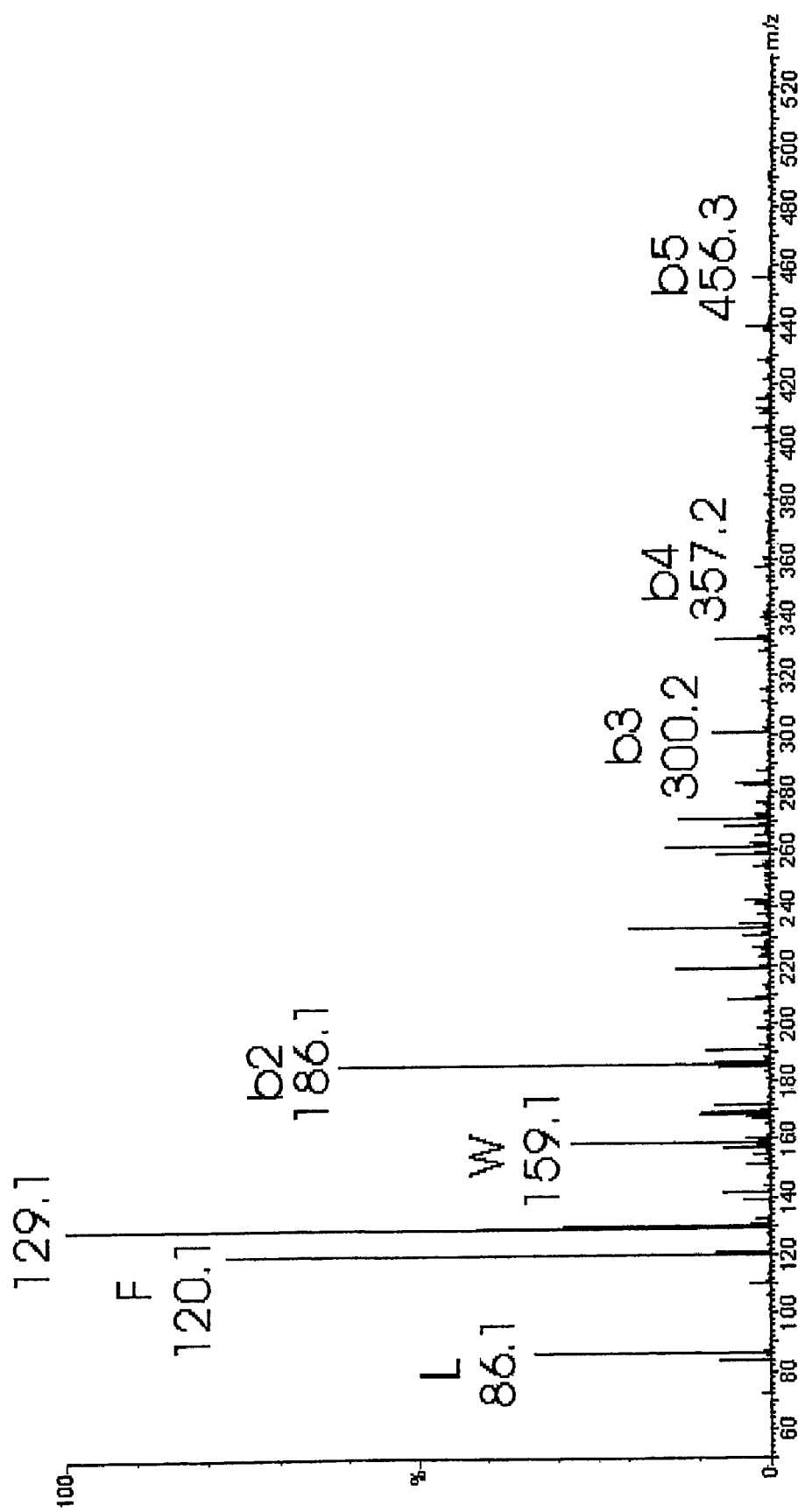
FIG. 6. MS/MS analysis of Streptococcus macedonicus ACA-DC 198 bacteriocin. (a) $b$ series ions obtained by fragmentation of the triply charged ion (m/z 932.8) and corresponding to the successive cleavage of the sequence from the N-terminal part; (b) Fragments in the high mass area of the MS/MS spectrum showing specific internal fragments. Fragments are named following the amino acid where-after the peptide bond is broken, together with the sequence stretch that is cleaved from the newly appearing N-terminus. Some y" ions, resulting from fragmentations at the C-terminus are observed as well.
Figure 6B:
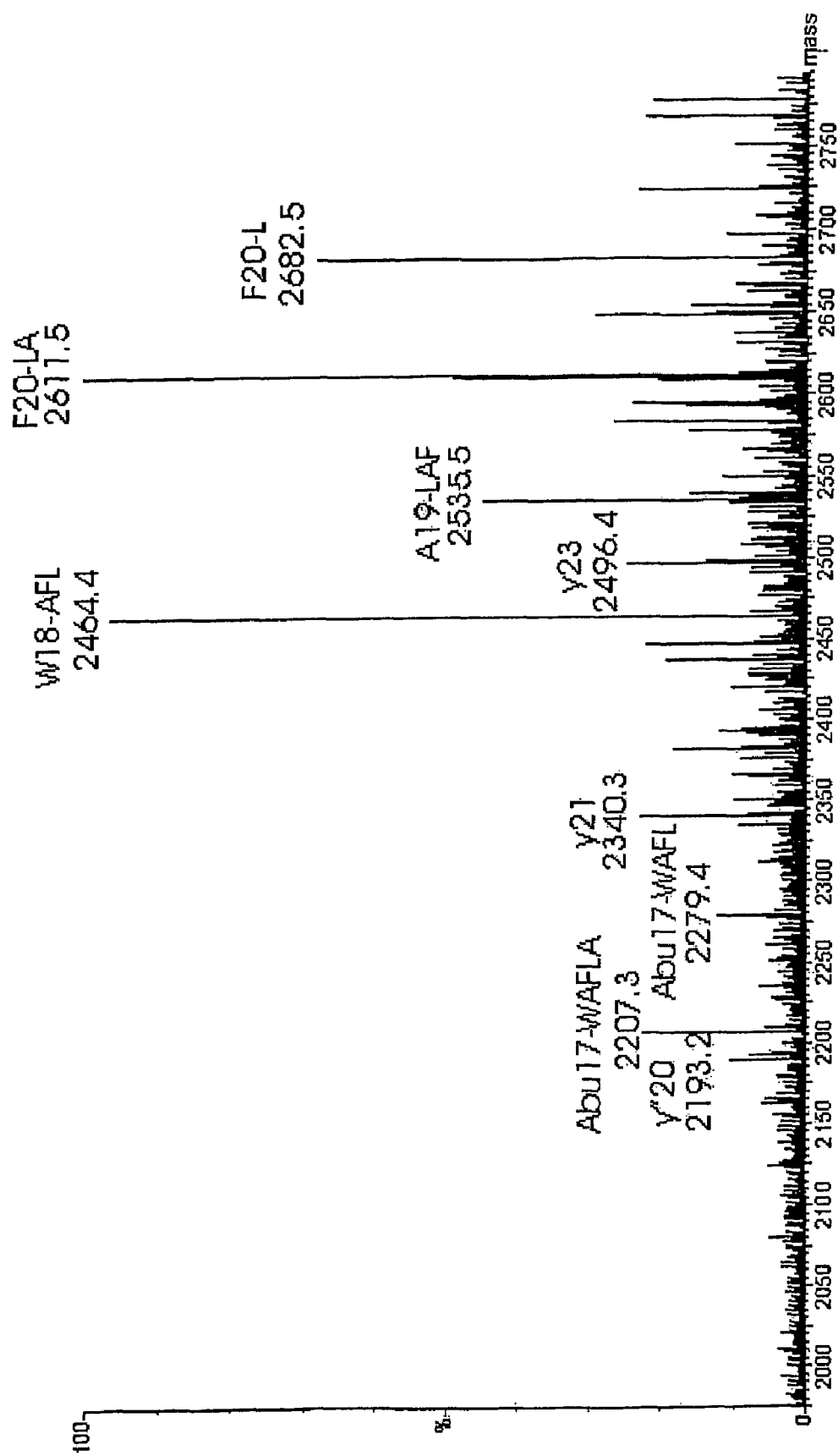

When the purified bacteriocin was analysed by electrospray ionization mass spectroscopy in the positive mode an average molecular mass of 2 794. 76±0.42 was calculated (FIG. 5). Mainly triple (m/z 932.8) and in quadruple (m/z 699.8) protonated molecular ions were observed. The triply protonated molecular ion (m/z 932.8) correlated well with the N-terminal sequence GKNGVFKDI (D stands for didehydrobutyrine or Dhb) of the SA-FF22 peptide (FIG. 4). The S. macedonicus ACA-DC 198 bacteriocin was further subjected to 0MS/MS. Fragmentation of the triply charged ion (m/z 932.8) yielded one b series ions. This series corresponded to the successive cleavage of the sequence from the N-terminal part (FIG. 6a). The observed singly charged product ions, m/z 186.1, 300.2 and 455, corresponded to the sequence GKNGV, which was consistent with the bacteriocin N-terminal sequence obtained by the Edman degradation method (FIG. 4). Furthermore, high mass fragments (FIG. 6b) indicate some "y" fragments, which are cleavages from the C-terminal part. Moreover several peaks are identified that are consistent with internal fragments due to double fragmentations. These cleavages occurred after the Abu17, Trp18, Ala19 and Phe20 combined with consecutive fragmentation of the newly appearing N-termini after this fragmentation site (Abu: aminobutyric acid), which indicates the crosslink between Abu17 and Cys25 in the SA-FF22 molecule [cleavage after F20 (-L or -LA), A19 (-FL), W18 (-AFL or -AFLA), and Abu17 (-WAFL or -WAFLA)]. Overall, weak fragmentation was observed, probably due to the presence of strong intra-chain linkages as is similarly seen for peptides involving disulfide bridges.

N-Terminal Amino Acid Sequencing

Purified sample of the bacteriocin was applied on a 476 A protein sequencer (Applied Biosystems, Foster City, Calif.). Homology searches were carried out with the protein databases of NCBI and Swiss-Prot (BLAST search, Altschul et al. 1990).

The Edman degradation revealed an amino acid sequence of 22 residues (SEQ ID NO 1, FIG. 4a). Eight out of these residues could not be identified (residues X). The reaction was blocked after the $22^{nd}$ cycle, indicating the existence of modified amino acids, such as lanthionine and methyllanthionine, which cannot be recognized by the Edman sequencing. Subsequent protein homology searches showed that the sequenced amino acids were identical to the respective amino acids of the lantibiotics SA-FF22 (SEQ ID NO 2, FIG. 4b) and SA-M49, both isolated from S. pyogenes strains (Hynes et al. 1993; Hynes et al. 1994; Jack et al. 1994).

Example 4

Effect of Growth Media on Macedocin Production

The effect of different growth media on both growth and bacteriocin production of S. macedonicus ACA-DC 198 was tested (Table 2). Subculturing and final growth was performed in the appropriate media at 37° C. Bacteriocin activity was determined in the cell-free culture supernatant at the end of the log phase, using the soft agar assay as described above with Lb. sakei subsp. sakei LMG $13558^T$ as indicator strain. To determine cell associated bacteriocin activity, the pH-dependent methods described by Tagg and Wannamaker (1978) and Yang et al. (1992) were applied during growth of S. macedonicus ACA-DC 198 in MRS broth.

During growth in skim milk supplemented with yeast extract (0.3%, wt/vol.), bacteriocin was determined in the cell free culture supernatant at various time intervals (3, 6, 9, 12 and 24 h), using the well diffusion assay as described above with L. lactis subsp. Lactis LMG $6890^T$ as indicator strain (FIG. 1).

The composition of the growth medium was critical for bacteriocin production by S. macedonicus ACA-DC 198. Indeed, S. macedonicus ACA-DC 198 grew well in all media tested. However, high bacteriocin activity was only detected when the strain was grown in skim milk, supplemented with nitrogen sources such as yeast extract, lactalbumin hydrolysate, tryptone, casein hydrolysate, and casamino acids at a concentration between 0.01 and 10% (wt/vol.) (Table 2). Increasing the concentration of lactalbumin hydrolysate or trypton to 1.5% (wt/vol) did not influence the bacteriocin production (400 AU/ml), while a slight increase was observed with yeast extract (300 AU/ml) or higher concentrations. On the other hand, increasing the concentration of casein hydrolysate or casamino acids slightly inhibited bacteriocin production by S. macedonicus ACA-DC 198.

Occasionally, activity was detected when growth took place in MRS broth. Moreover, no cell-associated bacterlocin activity was determined after applying pH-dependent extraction methods. Also, heating of the cell suspension to promote the desorption of cell-associated material did not result in any inhibitory activity. Finally, no bacteriocin production was observed in the other growth media tested.

Bacteriocin production in milk supplemented with yeast extract (0.3%, wt/vol) started at the early exponential growth phase, reached a maximum at the early stationary phase, and then remained constant, indicating primary metabolite kinetics (FIG. 1).

Example 5

Activity Spectrum of Macedocin

Effect of pH on Macedocin Activity

Purified bacteriocin (50 µl), pH 6, was mixed with 100 µl buffer (50 mM acetate pH 4.0 and 5.0; 50 mM potassium phosphate pH 6.0 and 7.0; 50 mM Tris-HCl pH 8.0 and 9.0), and incubated for 4 and 24 h, and for 1 week at 30° C. The bacteriocin activity was then determined, using the well diffusion assay with L. lactis subsp. lactis LMG $6890^T$ as described above.

Effect of Temperature on Macedocin Activity

Purified bacteriocin (pH 6) was heated for 1 h at 97° C. (heat block) and for 5, 10 and 20 min at 121° C. and 2.1 atm (autoclave). The bacteriocin activity was then determined as described above. Furthermore, purified bacteriocin was stored for 4 weeks at −70, −20, 4 and 30° C. The bacteriocin activity was determined at 1-week intervals, using the well diffusion assay as described above.

Effect of Enzymes on Macedocin Activity

Purified bacteriocin was incubated at 30° C. for 1, 4 and 24 h, in the presence of catalase, ficin and trypsin (0.05 M sodium phosphate buffer, pH 7.0), alpha-chymotrypsin, protease and proteinase K (0.05 M sodium phosphate buffer, pH 7.5), rennin (0.05 M sodium phosphate buffer, pH 6.0), and pepsin (0.2 M citric acid buffer, pH 2.0), at a final concentration of 2 mg/ml (all enzymes were purchased from Sigma). Purified bacteriocin in buffer without enzyme, enzyme/buffer solutions, and buffers only were used as controls. The bacteriocin activity was then determined, using the well diffusion assay as described above.

Results: Effect of pH, Temperature and Enzymes on the Bacteriocin Activity

Even after one week of incubation at 30° C. at various pH values from 4 to 9, the bacteriocin produced by S. macedonicus ACA-DC 198 retained full activity. Additionally, the bacteriocin was found to be very stable to heat, as no activity loss was observed after incubation for 1 h at 97° C., or even after 20 min at 121° C. and 2.1 atm of overpressure. Finally, storage for 4 weeks at −70, −20, 4 and 30° C., did not affect bacteriocin activity.

The bacteriocin was resistant to catalase. Proteolytic enzymes, such as α-chymotrypsin, proteinase K and protease, inactivated the bacteriocin after 1 h of incubation, while ficin did after 4 h. Treatment with rennin and trypsin resulted in full inactivation only after 24 h. This makes macedocin particularly interesting in cheese fermentations. Among the proteolytic enzymes tested, only pepsin did not affect bacteriocin activity after 24 h of treatment.

The resistance of the purified molecule to catalase excluded antimicrobial activity mediated by hydrogen peroxide. Furthermore, its sensitivity to various proteolytic enzymes confirmed its proteinaceous nature. The data from the purification procedure suggested that the S. macedonicus ACA-DC 198 bacteriocin is a cationic and highly hydrophobic peptide. These are all common characteristics for many bacteriocins produced by lactic acid bacteria, and in particular, lantibiotics and Class II bacteriocins (Klaenhammer 1993; Ennan et al. 2000; McAuliffe et al. 2001).

Example 6

Effect of Physical Factors on Macedocin Production Through Fermentation

To investigate the influence of temperature and pH on both growth and macedocin production of S. macedonicus ACA-DC 198, a series of fermentations was performed with milk production medium (MP), consisting of sterile skim milk (10% of low heat skim milk powder, wt/vol; Belgomilk, Kallo, Belgium) supplemented with 0.3% (wt/vol.) yeast extract (Merck). Fermentations were carried out in a 15-liter laboratory fermentor (Biostat C; B. Braun Biotech International, Melsungen, Germany) containing 10 liters of MP. The vessel was sterilized in situ at 121° C. for 20 min. Both milk and yeast extract were sterilized separately in an autoclave (121° C. for 20 min), and aseptically added to the fermentor. For the preparation of the inoculum, 10 ml of MP was inoculated with 0.5 ml of a freshly prepared S. macedonicus ACA-DC 198 culture (obtained by propagating a culture, stored at −80° C., twice in MP), and incubated for 12 h at 37° C. One ml of this preculture was added to 100 ml of MP. After again 12 h of growth at 37° C. this culture was used to inoculate the fermentor (1%, vol./vol.). Temperature and pH control was performed on-line (Micro-MFCS for Windows NT; B. Braun Biotech International). The pH was controlled to within pH 0.05 of the set point by automatic addition of 15 M NaOH. Temperature stayed within 0.1° C. of the set point. Moderate agitation (100 rpm) was performed to ensure homogeneity of the broth.

During the first experiments the pH was maintained constant at pH 6.5 while the fermentations were carried out at 20° C., 25° C., 30° C., 37° C., 42° C., and 45° C. In a second series of experiments the temperature was held constant at 30° C. while the fermentations were carried out with constant pH values of 5.1, 5.5, 6.0, 6.5, and 6.9.

Samples were withdrawn aseptically from the fermentor to determine optical density at 480 nm according to the method of Kanasaki et al. (1975), and bacteriocin activity. The maximum specific growth $\mu_{max}$ was calculated from the slope of a linear plot of in (OD/OD$_0$) versus time, where OD$_0$ is the optical density at the start of the fermentation and OD at a certain time point.

Results

Figure 7:
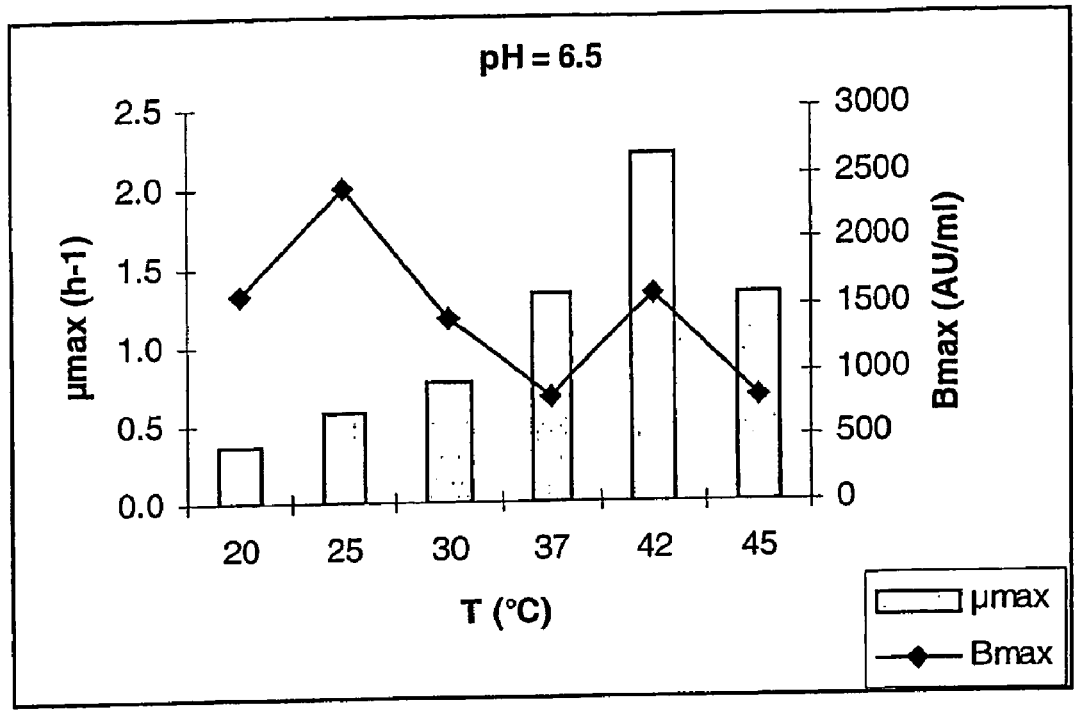
FIG. 7. Influence of temperature at a constant pH of 6.5 on the maximum specific growth rate ($\mu_{max}$, in $h^{-1}$) and the maximum volumetric bacteriocin activity ($B_{max}$, in AU/ml) of S. macedonicus ACA-DC 198 growth and bacteriocin production in MP medium (10% skim milk powder, wt/vol; 0.3% yeast extract, wt/vol).

FIG. 7 demonstrates the influence of temperature at a constant pH of 6.5 on the maximum specific growth rate ($\mu_{max}$) and maximum bacteriocin activity ($B_{max}$). It indicates that growth is maximal at 42° C., while volumetric bacteriocin activity decreases with increasing temperature.

Figure 8:
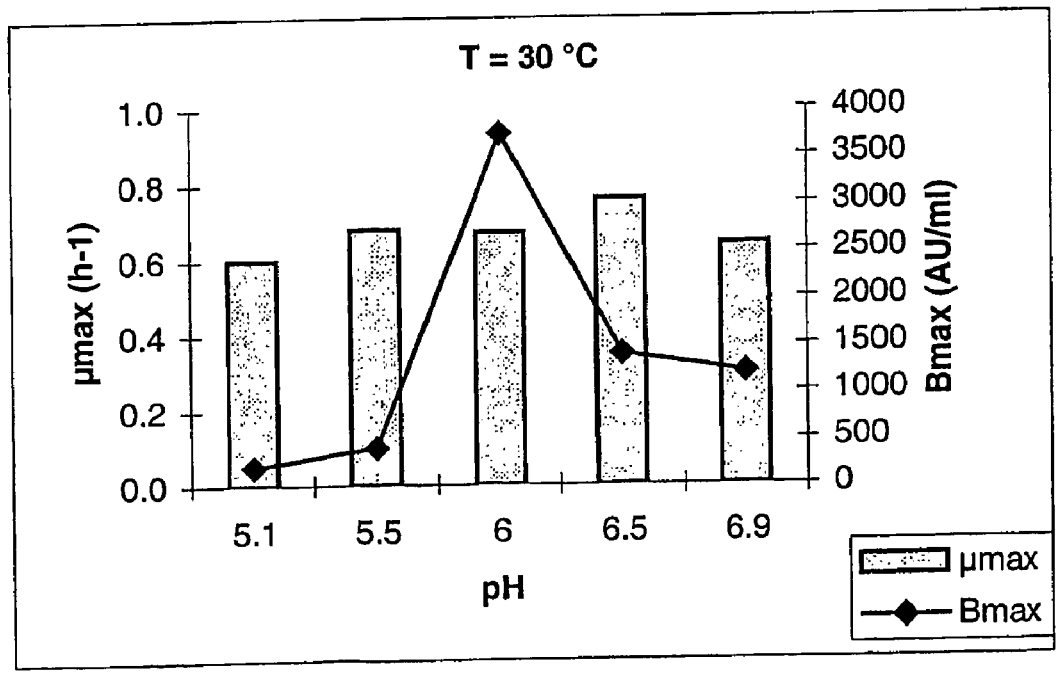
FIG. 8. Influence of a constant pH at a controlled temperature of 30° C. on the maximum specific growth rate ($\mu_{max}$, in $h^{-1}$) and the maximum volumetric bacteriocin activity ($B_{max}$, in AU/ml) of S. macedonicus ACA-DC 198 growth and bacteriocin production in MP medium (10% skim milk powder, wt/vol; 0.3% yeast extract, wt/vol).

FIG. 8 demonstrates the influence of a constant pH at a controlled temperature of 30° C. A maximal $\mu_{max}$ occurred in a broad pH range of growth; a maximal volumetric bacteriocin activity occurred around pH 6.0.

REFERENCES

Altschul, S. F., Gish, W., Miller, W., Myers, E. W. & Lipman, D. J. (1990) Basic local alignment search tool. *J. Mol. Biol.* 215, 403-410.

Biswas, S. R., Ray, P., Johnson, M. C. & Ray, B. (1991) Influence of growth conditions on the production of a bacteriocin, pediocin AcH, by *Pediococcus acidilactici* H. *Appl. Environ. Microbiol.* 57,4, 1265-1267.

De Man, J. C., M. Rogosa, and M. E. Sharpe. (1960). A medium for the cultivation of *lactobacilli. J. Appl. Ind. Bacteriol.* 23:130-135.

De Vuyst, L. (1995) Nutritional factors affecting nisin production by *Lactococcus lactis* subsp. *lactis* NIZO 22186 in a synthetic medium. *J. Appl. Bacteriol.* 78, 28-33.

De Vuyst L. & Vandamme E. J. (1994) Antimicrobial potential of lactic acid bacteria. In Bacteriocins of lactic acid bacteria, L. De Vuyst & E. J. Vandamme eds., Blackie Academic & Professional, London De Vuyst, L., Callewaert, R. & Pot, B. (1996) Characterization of the antagonistic activity of *Lactobacillus amylovorous* DCE 471 and the large scale isolation of its bacteriocin Amylovorin L471. *System. Appl. Microbiol.* 19, 9-20.

Enan, G. (2000) Inhibition of *Bacillus sereus* ATCC 14579 by plantaricin UG1 in vitro and in food. *Nahrung.* 44,5, 364-377.

Georgalaki, M. D., Sarantinopoulos, P., Ferreira, E. S., De Vuyst, L., Kalantzopoulos, G., & Tsakalidou, E. (2000). Metabolic Properties of *Streptococcus macedonicus* strains isolated from Greek Kasseri cheese. *J. Appl. Microbiol.* 88, 817-825.

Hardie, J. M. (1986) Genus *Streptococcus*. In Bergey's Manual of Systematic Bacteriology, vol. 2 ed. P. H. A.

Sneath, N. S. Mair, M. E. Sharpe & J. G. Holt. The Williams and Wilkins Co., Baltimore, pp. 1043-1071.

Hynes, W. L., Ferretti, J. J. & Tagg, J. R. (1993) Cloning of the gene encoding streptococcin A-FF22, lantibiotic produced by *Streptococcus pyogenes*, determination of its nucleotide sequence. *Appl. Environ. Microbiol.* 59,6, 1969-1971.

Hynes, W. L., Friend, V. L. & Ferretti, J. J. (1994) Duplication of the lantibiotic structural gene in M-type 49 group A streptococcus strains producing streptococcin A-M49. *Appl. Environ. Microbiol.* 60,11, 4207-4209.

Jack, R. W., Carne, A., Metzger, J., Stefanovic, S., Sahl, H.-G., Jung, G. & Tagg, J. (1994) Elucidation of the structure of SA-FF22, a lanthionine-containing antibacterial peptide produced by *Streptococcus pyogenes* strain FF22. *Eur. J. Biochem.* 220,2, 455-462.

Kanasaki, M., Breheny, S., Hillier, A. J. & Jago, G. R. (1975) Effect of temperature on the growth and acid production of lactic acid bacteria. 1. A rapid method for the estimation of bacterial populations in milk. *Aust. J. Dairy Technol.* 30,4, 142-144.

Klaenhammer, T. R. (1993) Genetics of bacteriocins produced by lactic acid bacteria. *FEMS Microbiol. Rev.* 12, 39-86.

Loyola-Rodriguez, J. P., Morisaki, I., Kitamura, K. & Hamada, S. (1992) Purification and properties of extracellular mutacin, a bacteriocin from *Streptococcus sobrinus*. *J. Gen. Microbiol.* 138,2, 269-274.

McAuliffe, O., Paul Ross, R. & Hill, C. (2001) Lantibiotics: structure, biosynthesis and mode of action. *FEMS Microbiol Rev.* 25, 285-308.

Novák, J., Caufield, P. W., & Miller, E. J. (1994) Isolation and biochemical characterization of a novel lantibiotic mutacin from *Streptococcus mutans*. J. Bacteriol. 176,14, 4316-4320.

Parker, M. T. (1983) *Streptococcus* and *Lactobacillus*. In Wilson, Miles and Parker (Editors), Topley and Wilson's Principles of Bacteriology, Virology and Immunity, Seventh Edition, Volume 2, Edward Arnold, London, pp. 173-217.

Raibaud, P., Caulet, M., Galpin, J. V. and Moquot, G. (1961). Studies on the bacterial flora of the alimentary tract of pigs. II-Streptococci: Selective enumeration and differentiation of the dominant group. Journal of Applied Bacteriology, 24, 285-306.

Rogers, L. A. (1928) The inhibiting effect of *Streptococcus lactis* on *Lactobacillus bulgaricus*. J. Bacteriolo. 16, 321-325.

Tagg, J. R., Read, R. S. D. & McGiven, A. R. (1973) Bacteriocin of a group A streptococcus: partial purification and properties. *Antimicrob. Agents Chemother.* 4, 214-221.

Tagg, J. R. Dajani, A. S. and Wannamaker, L. W. (1976). Bacteriocins of Gram-positive bacteria. *Bacteriol. Rev.* 40, 722-756.

Tagg, J. R., and Wannamaker, L. W. (1978). Streptococcin A-FF22: Nisin-like antibiotic substance produced by a group A streptococcus. *Antimicrob. Agents Chemother.* 14:36-39.

Tsakalidou, E., Zoidou, E., B. Pot, B., Wassil, L., Ludwig, W., Devriese, L. A., Kalantzopoulos, G., Schleifer, K. H. & Kersters, K. (1998) Identification of streptococci from Greek Kasseri cheese and description of *Streptococcus macedonicus* sp. nov. *Int. J. Syst. Bacteriol.* 48, 519-527.

Vignolo, G. M., de Kairuz, M. N., de Ruiz Holgado, A. A. P. & Oliver, G. (1995) Influence of growth conditions on the production of lactocin 705, a bacteriocin produced by *Lactobacillus casei* CRL 705. *J. Appl. Bacteriol.* 78, 5-10.

Yang, R., Johnson, M. C., and Ray, B. (1992) Novel method to extract large amounts of bacteriocins from lactic acid bacteria. *Appl. Environm. Microbiol.* 58:3355-3359.

Walstra, P., Noomen, A. and T. J. Geurts. 1993. Dutch-type varieties, p. 75. In P. F. Fox (ed.), Cheese: Chemistry, Physics and Microbiology, Second Edition, vol. 2. Chapman and Hall, London, U.K.

---

What is claimed is:

1. A method for producing the food grade lantibiotic, macedocin, comprising growing a *Streptococcus macedonicus* ACA-DC 198 strain, deposited under BCCM™/LMG Accession No. LMG-P-21771, in a growth medium comprising 10% wt/vol skim milk supplemented with at least one of the following: 0.01 to 9% (wt/vol) yeast extract, 0.3 to 1.5% (wt/vol) tryptone, 0.3 to 6.0% (wt/vol) lactalbumin hydrolysate, 0.3% casamino acids (wt/vol), or 0.3% casein hydrolysate to produce a culture; and at least partially purifying the food grade macedocin from the culture.

* * * * *

UNITED STATES PATENT AND TRADEMARK OFFICE
CERTIFICATE OF CORRECTION

PATENT NO. : 7,449,311 B2
APPLICATION NO. : 10/495105
DATED : November 11, 2008
INVENTOR(S) : De Vuyst et al.

It is certified that error appears in the above-identified patent and that said Letters Patent is hereby corrected as shown below:

Title page page 1, Column 2, Other Publications, Line 8, "*Steptococcus pyrogenes*" should be changed to --*Streptococcus pyrogenes*--

Columns 3-4, Lines 56-67 and 1-7, "*S. pyogenes* belongs...as described earlier" should be a separate paragraph Column 8, Line 4, ""Fermented product"" should be changed to --"fermented product"--

Column 12, Line 2, "and substance P." should be changed to --and substance P,--

Column 12, Line 19, "of 2 794.76±0.42 Da." should be changed to --of 2794.76±0.42 Da.--

Column 12, Line 21, "(a) b series ions" should be changed to --(a) *b* series ions--

Column 12, Line 44, "198 bacteriocin" should be changed to --198 bacteriocin.--

Columns 13-14, Table 1, Line 71, "microoerophilic" should be changed to --microaerophilic--

Column 19, Line 56, "Quantitavive Determination" should be changed to --Quantitative Determination--

Column 20, Line 65, "(50% saturatation" should be changed to --(50% saturation--

Column 21, Line 24, "(1 m/l)," should be changed to --1 ml/l),--

Column 22, Line 42, "purified bacterlocin" should be changed to --purified bacteriocin--

Column 23, Line 32, "(McAufiffe et al., 2001)," should be changed to --(McAuliffe et al., 2001),--

Column 24, Line 39-40, "of Schäagger and" should be changed to --of Schägger and--

Column 25, Line 27, "to 0MS/MS." should be changed to --to MS/MS.--

Column 26, Line 38, "cell-associated bacterlocin" should be changed to --cell-associated bacteriocin--

Signed and Sealed this

Twenty-fifth Day of May, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 22
<212> TYPE: PRT
<213> ORGANISM: Streptococcus macedonicus
<220> FEATURE:
<221> NAME/KEY: VARIANT
<222> LOCATION: (1)...(22)
<223> OTHER INFORMATION: Xaa = Any Amino Acid

<400> SEQUENCE: 1

Gly Lys Asn Gly Val Phe Lys Xaa Ile Xaa His Glu Xaa His Xaa Asn
1               5                   10                  15

Xaa Xaa Xaa Phe Xaa Ala
            20

<210> SEQ ID NO 2
<211> LENGTH: 26
<212> TYPE: PRT
<213> ORGANISM: Streptococcus pyogenes
```

```
<400> SEQUENCE: 2

Gly Lys Asn Gly Val Phe Lys Thr Ile Ser His Glu Cys His Leu Asn
1               5                   10                  15

Thr Trp Ala Phe Leu Ala Thr Cys Cys Ser
            20                  25
```